United States Patent
Igawa et al.

(10) Patent No.: US 11,591,513 B2
(45) Date of Patent: Feb. 28, 2023

(54) ORGANIC COMPOUND, ELECTROCHROMIC DEVICE, ELECTROCHROMIC APPARATUS, OPTICAL FILTER, IMAGE PICKUP APPARATUS, LENS UNIT, AND WINDOW MEMBER

(71) Applicant: CANON KABUSHIKI KAISHA, Tokyo (JP)

(72) Inventors: Satoshi Igawa, Fujisawa (JP); Jun Yamamoto, Tokyo (JP); Kenji Yamada, Yokohama (JP); Tetsuya Tamura, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1210 days.

(21) Appl. No.: 16/125,526

(22) Filed: Sep. 7, 2018

(65) Prior Publication Data
US 2019/0002758 A1  Jan. 3, 2019

Related U.S. Application Data

(63) Continuation of application No. PCT/JP2017/007923, filed on Feb. 28, 2017.

(30) Foreign Application Priority Data

Mar. 10, 2016 (JP) .............................. JP2016-047058
Mar. 10, 2016 (JP) .............................. JP2016-047059
Feb. 20, 2017 (JP) .............................. JP2017-029313

(51) Int. Cl.
*C09K 9/02* (2006.01)
*G02F 1/15* (2019.01)
(Continued)

(52) U.S. Cl.
CPC .............. *C09K 9/02* (2013.01); *C07D 401/04* (2013.01); *C07D 471/04* (2013.01);
(Continued)

(58) Field of Classification Search
CPC .............. C09K 9/02; C09K 2211/1018; C07D 401/04; C07D 471/04; C07D 471/14;
(Continued)

(56) References Cited

U.S. PATENT DOCUMENTS 5,294,376 A  3/1994 Byker
6,661,559 B2 12/2003 Byker et al.

FOREIGN PATENT DOCUMENTS

CN  1341232 A   3/2002
CN  104804720 A  7/2015
(Continued)

OTHER PUBLICATIONS

Xiaoyuan Li, et al., Layer-by-layer Assembled Molecular Films-I: Organic-Inorganic Hybrid Films and Electrocatalytic Sensing Applications, Mol. Cryst. And Liq. Cryst., 2001, pp. 1-4, vol. 371.

(Continued)

*Primary Examiner* — Bijan Ahvazi
(74) *Attorney, Agent, or Firm* — Canon U.S.A., Inc. IP Division

(57) ABSTRACT

An organic compound is represented by general formula (1) below:

(Continued)

where $X_1$ and $X_2$ are each independently selected from the group consisting of an alkyl group, an aryl group, and an aralkyl group;

$R_{11}$ to $R_{16}$ are each independently selected from the group consisting of a hydrogen atom, an alkyl group, an alkoxy group, an aryl group, a heterocyclic group, and a halogen atom; $R_{21}$ and $R_{22}$ are each independently selected from the group consisting of a hydrogen atom, an alkyl group, an aryl group, and an aralkyl group; and $A_1^-$ and $A_2^-$ each independently represent a monovalent anion.

11 Claims, 10 Drawing Sheets

(51) Int. Cl.
| | |
|---|---|
| E06B 3/67 | (2006.01) |
| E06B 9/24 | (2006.01) |
| C07D 471/04 | (2006.01) |
| C07F 9/576 | (2006.01) |
| G02F 1/1516 | (2019.01) |
| G02F 1/1503 | (2019.01) |
| C07D 401/04 | (2006.01) |
| C07D 471/14 | (2006.01) |
| C07D 471/16 | (2006.01) |
| C07F 9/6561 | (2006.01) |
| C07F 9/6584 | (2006.01) |
| G02F 1/1514 | (2019.01) |
| H04N 5/225 | (2006.01) |

(52) U.S. Cl.
CPC ......... *C07D 471/14* (2013.01); *C07D 471/16* (2013.01); *C07F 9/5765* (2013.01); *C07F 9/6584* (2013.01); *C07F 9/65616* (2013.01); *E06B 3/6722* (2013.01); *E06B 9/24* (2013.01); *G02F 1/1503* (2019.01); *G02F 1/1516* (2019.01); *C09K 2211/1018* (2013.01); *C09K 2211/1022* (2013.01); *C09K 2211/1044* (2013.01); *C09K 2211/1055* (2013.01); *E06B 2009/2464* (2013.01); *G02F 2001/15145* (2019.01); *H04N 5/2254* (2013.01)

(58) Field of Classification Search
CPC .. C07D 471/16; C07F 9/6584; C07F 9/65616; H04N 5/2254; G02F 1/1521; G02F 2001/1512; E06B 3/6722; E06B 9/24
See application file for complete search history.

(56) References Cited

FOREIGN PATENT DOCUMENTS

| | | | |
|---|---|---|---|
| DE | 19825371 | A1 | 12/1999 |
| DE | 102012201673 | A | 8/2013 |
| EP | 0431547 | A2 | 6/1991 |
| EP | 1030212 | A2 | 8/2000 |
| GB | 1507834 | A | 4/1978 |
| JP | S5168793 | A | 6/1976 |
| JP | S51068793 | A | 6/1976 |
| JP | S5437078 | A | 3/1979 |
| JP | S54160572 | A | 12/1979 |
| JP | 2001519922 | A | 10/2001 |
| JP | 2016-155802 | A | 9/2016 |
| JP | 2017197477 | A * | 11/2017 ........... C07D 405/14 |
| WO | 0014172 | A1 | 3/2000 |
| WO | 2011/046222 | A1 | 4/2011 |
| WO | 2016/006204 | A1 | 1/2016 |

OTHER PUBLICATIONS

Bruna Clara De Simone, et al., TDDFT Investigation on Methylviologen, 3,7-diazabenzophospole, and Helical Helquat Elecrochromic Systems, Theor Chem Acc, Apr. 11, 2016, pp. 1-9, 135: 118.

Christian Reus, A Convenient N-Arylation Route for Electron-Deficient Pyridines: The Case of π-Extended Electrochromic Phosphaviologens, J. Am. Chem. Soc., Sep. 1, 2015, pp. 11710-11717, 137(36).

Monika Stolar, Synthesis and Tunability of Highly Electron-Accepting, N-Benzylated "Phosphaviologens", J Am. Chem. Soc., Mar. 2, 2015, pp. 3366-3371, 137(9).

M.H. Miles, et al., Electrochromic Studies of Viologen, Tungsten Trioxide, Polyaniline, and Prussion Blue Materials, Proceedings-Electrochemistry Society, pp. 137-156.

Electrochromism of diquat bis(tetrafluoroborate), Zhurnal Prikladnoi Spektroskopii, pp. 1020-1022, 39(6).

Enrique Botana, et al., Inclusion of Cavitands and Calix[4]arenes into a Metallobridged para-(1H-Imidazo[4,5-f][3,8]phenanthrolin-2-yl)-Expanded Calix[4]arene, Angew. Chem. Int. Ed., 2007, pp. 198-201, 46, Wiley-VCH Veriag GmbH & Co. KGaA, Weinheim.

Stefan Durben, et al., 3,7-Diazadibenzophosphole Oxide: A Phosphorus-Bridged Viologen Analogue with Significantly Lowered Reduction Threshold, Angew. Chem. Int. Ed., 2011, pp. 7948-7952, 50, Wiley-VCH Verlag GmbH & Co. KGaA, Weinheim.

Zhurnal Prikladnoi Spektroskopii, Electrochromism of diquat diboronfluoride, Journal of Applied Spectroscopy, Dec. 1983, pp. 1020-1022, vol. XXXIX, Issue 6, ISSN 0514-7506.

\* cited by examiner

ORGANIC COMPOUND, ELECTROCHROMIC DEVICE, ELECTROCHROMIC APPARATUS, OPTICAL FILTER, IMAGE PICKUP APPARATUS, LENS UNIT, AND WINDOW MEMBER

CROSS-REFERENCE TO RELATED APPLICATIONS

This application is a Continuation of International Patent Application No. PCT/JP2017/007923, filed Feb. 28, 2017, which claims the benefit of Japanese Patent Application No. 2016-047059, filed Mar. 10, 2016, Japanese Patent Application No. 2016-047058, filed Mar. 10, 2016, and Japanese Patent Application No. 2017-029313, filed Feb. 20, 2017, all of which are hereby incorporated by reference herein in their entirety.

TECHNICAL FIELD

The present invention relates to an electrochromic organic compound, an electrochromic device, an electrochromic apparatus, an optical filter, an image pickup apparatus, a lens unit, and a window member.

BACKGROUND ART

An electrochromic phenomenon (EC phenomenon) is a phenomenon in which a reversible electrochemical reaction (oxidation-reduction reaction) induced upon application of voltage changes the light absorption range of a material and thus the material is colored or decolored. An electrochemically colored/decolored device that uses such an EC phenomenon is referred to as an electrochromic device (EC device) and is promising for application as a light-controlling device with varying light transmittance. An organic EC device in which an electrochromic (EC) low-molecular-weight organic material that exhibits an electrochromic phenomenon is colored/decolored in a solution state is known to have advantages of a sufficient contrast ratio in a colored state and high transmittance in a decolored state.

PTL 1 discloses that a phenazine derivative is used as an anode EC material and a bipyridine derivative such as a viologen derivative is used as a cathode EC material. PTL 1 also discloses examples of the structure of a bipyridine derivative having electrochromism.

PTL 2 discloses an organic compound of a pyridine derivative that is colored in a reduction state. PTL 2 also discloses an electrochromic device that is colored in cyan, magenta, or yellow.

PTL 3 discloses an electrochromic device including various viologen derivatives colored in a reduction state.

CITATION LIST

Patent Literature

PTL 1: U.S. Pat. No. 5,294,376
PTL 2: International Publication No. 2011/046222
PTL 3: PCT Japanese Translation Patent Publication No. 2001-519922

When such an EC device is applied to, for example, full-color displays and color filters, a large change in the wavelength selectivity (shape of absorption spectrum) of light absorption due to an operating environment needs to be prevented. However, in electrochromic devices having a bipyridine structure such as a bipyridine derivative, the absorption spectrum of the bipyridine derivative changes in accordance with the ambient temperature during driving, which sometimes changes the absorption spectrum of the EC device.

In view of the foregoing, it is an object of the present invention to provide an EC organic compound or EC device in which the change in the absorption spectrum in a colored state at different ambient temperatures can be reduced compared with the related art.

SUMMARY OF INVENTION

An organic compound according to one aspect of the present invention is represented by general formula (1) below.

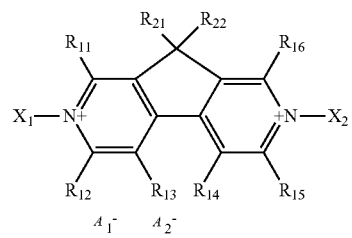

(1)

In the general formula (1), $X_1$ and $X_2$ are each independently selected from the group consisting of an alkyl group optionally having a substituent, an aryl group optionally having a substituent, and an aralkyl group optionally having a substituent. $R_{11}$ to $R_{16}$ are each independently selected from the group consisting of a hydrogen atom, an alkyl group optionally having a substituent, an alkoxy group optionally having a substituent, an aryl group optionally having a substituent, a heterocyclic group optionally having a substituent, and a halogen atom. $R_{21}$ and $R_{22}$ are each independently selected from the group consisting of a hydrogen atom, an alkyl group optionally having a substituent, an aryl group optionally having a substituent, and an aralkyl group optionally having a substituent; and $A_1^-$ and $A_2^-$ each independently represent a monovalent anion. An electrochromic device according to another aspect of the present invention includes a pair of electrodes and an electrochromic layer that is disposed between the pair of electrodes and contains an anodic compound and a cathodic compound, wherein the electrochromic layer contains a bipyridine derivative and the electrochromic layer satisfies formula (1) in a wavelength range of 450 nm or more and 650 nm or less:

$$0.6 < f2(m)/f1(m) < 1.4 \qquad (1)$$

where f1(m) represents a value obtained by normalizing an absorbance of the electrochromic layer in a colored state at an ambient temperature of 0° C. at a wavelength m of 450 nm or more and 650 nm or less with respect to an absorbance at a wavelength at which the bipyridine derivative exhibits radical absorption, and f2(m) represents a value obtained by normalizing an absorbance of the electrochromic layer in a colored state at an ambient temperature of 80° C. at a wavelength m of 450 nm or more and 650 nm or less with respect to an absorbance at a wavelength at which the bipyridine derivative exhibits radical absorption.

Further features of the present invention will become apparent from the following description of exemplary embodiments with reference to the attached drawings.

DESCRIPTION OF EMBODIMENTS

In general, electrochromic devices (hereafter referred to as "EC devices") preferably have an absorption spectrum that does not change even when the ambient temperature is changed, for example, by generation of heat from an apparatus including the EC device or by seasonal or areal factors.

When a bipyridine derivative such as a viologen derivative is used as a cathode EC material, one of causes of a change in the absorption of the bipyridine derivative is believed to be formation of a dimer (associate) through association of radical species of the bipyridine derivative generated by an electrode reaction. That is, in the bipyridine derivative, the existence ratio of monomer and associate sometimes changes with the ambient temperature. Associates of radical species have an electronic state different from that of monomers of radical species and thus have a different absorption spectrum. Therefore, if the existence ratio of monomer and associate changes with the ambient temperature, the absorption spectrum of an EC device changes.

In view of the foregoing, in the following embodiments, an EC compound and an EC device that have only a small change in absorption spectrum even if the ambient temperature changes are provided. As a result, there can be provided an EC device capable of performing gradation control while the change in absorption spectrum is reduced even if the ambient temperature changes, and an EC apparatus, an optical filter, an image pickup apparatus, a lens unit, and a window member that include the EC device.

First Embodiment

EC Device

Figure 1:
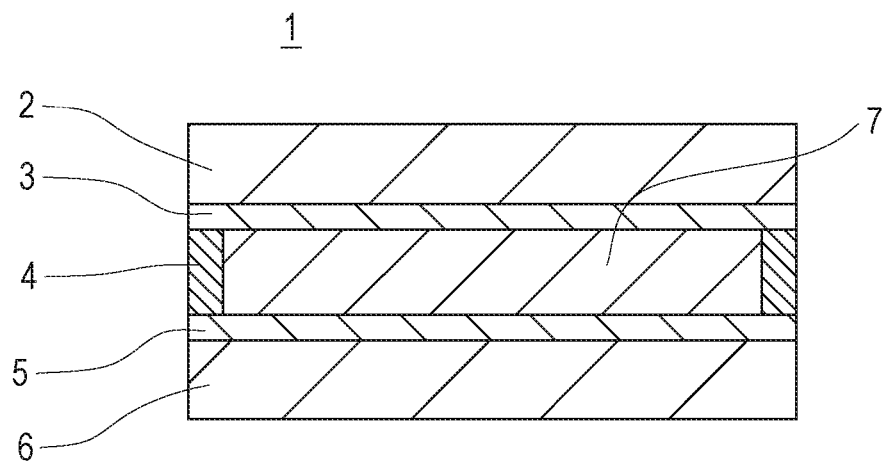
FIG. 1 schematically illustrates a structure of an electrochromic device according to a first embodiment.

FIG. 1 schematically illustrates an example of a structure of an electrochromic device 1 (hereafter referred to as an "EC device 1") according to this embodiment. The EC device 1 according to this embodiment includes substrates 2 and 6, a pair of electrodes 3 and 5, and an electrochromic layer 7 (hereafter referred to as an "EC layer 7").

The pair of electrodes 3 and 5 are disposed between a pair of substrates 2 and 6. A pair of substrates 2 and 6 on which electrode films serving as the electrodes 3 and 5 are bonded to each other with spacers 4 disposed therebetween so that the electrodes 3 and 5 face each other. The EC device 1 includes an EC layer 7 disposed in a gap defined by the pair of electrodes 3 and 5 and the spacers 4. The EC device 1 according to this embodiment includes the substrates 2 and 6, the electrodes 3 and 5, the spacers 4, and the EC layer 7. The EC device includes at least a pair of electrodes and an EC layer disposed between the pair of electrodes, and does not necessarily include substrates and spacers.

The spacers 4 are disposed between the pair of electrodes 3 and 5 so as to provide a space for accommodating the EC layer 7 containing a solution containing an EC organic compound. The spacers 4 can be made of a material such as polyimide, polytetrafluoroethylene, fluororubber, or epoxy resin. With these spacers 4, a certain distance can be kept between the electrodes 3 and 5.

The EC device 1 may have a liquid injection port (not illustrated) that is formed by the pair of electrodes 3 and 5 and the spacers 4. A composition having an EC organic compound is injected from the liquid injection port. Then, the injection port is covered with a sealing member and hermetically sealed with an adhesive or the like. Thus, a device can be produced. The sealing member also has a role of separating the adhesive from the EC organic compound. The shape of the sealing member is not particularly limited, but is preferably a tapered shape such as a wedge shape.

A method for forming the EC device 1 according to this embodiment is not particularly limited. For example, the EC device 1 can be formed by injecting a liquid containing an EC organic compound prepared in advance into a gap formed between electrode substrates serving as the pair of electrodes 3 and 5 by, for example, a vacuum injection method, an atmospheric injection method, or a meniscus method to form an EC layer 7.

The EC layer 7 contains at least one anode EC material and at least one cathode EC material. By applying voltage between the electrodes 3 and 5, the EC materials cause an electrochemical reaction. The EC device 1 according to this embodiment is a complementary EC device in which the EC layer 7 contains at least one anode EC material and at least one cathode EC material. The mutual EC device does not necessarily have a structure in which at least one anode EC material and at least one cathode EC material are contained in the EC layer as long as transfer of electrons occurs between the anode material and the cathode material. For example, the complementary EC device may have a structure including at least one cathode EC material and an anode material with no electrochromism or a structure including at least one anode EC material and a cathode material with no electrochromism.

In general, when no voltage is applied, an organic EC material is in a neutral state and does not exhibit absorption in a visible region. In such a decolored state, the organic EC device has high light transmittance. When voltage is applied between electrodes, an electrochemical reaction occurs in the organic EC material, resulting in a change from the neutral state to an oxidation state (cation) or a reduction state (anion). The organic EC material exhibits absorption in a visible region in a state of cation or anion and undergoes coloring. In such a colored state, the organic EC device has low light transmittance. A material, such as a viologen derivative, that forms a transparent dication structure in an initial state and is colored through formation of radical species by one-electron reduction is also used.

Hereafter, the discussion will be made while the light transmittance of the EC device 1 is replaced with the absorbance of the EC device 1. The transmittance and the absorbance have the relationship −LOG(transmittance)=(absorbance). The absorbance increases by about 0.3 each time when the transmittance is halved.

Substrate

When the EC device 1 is used as a light-controlling device, high transmittance is preferably kept in a decolored state to reduce an influence on an optical system. Therefore, the substrates 2 and 6 are preferably transparent substrates that sufficiently transmit visible light and are generally made of a glass material. An optical glass substrate such as Corning #7059 or BK-7 can be suitably used. A material such as plastic or ceramic can also be appropriately used as long as the material has sufficient transparency. In this embodiment, the transparency means that the transmittance of visible light is 90% or more.

The substrates 2 and 6 are preferably made of a rigid material with less strain. The substrates 2 and 6 are more preferably substrates with less flexibility. The substrates 2 and 6 generally have a thickness of several tens of micrometers to several millimeters.

Electrode

When the EC device 1 is used as a light-controlling device, high transmittance is preferably kept in a decolored state to reduce an influence on an optical system. Therefore, the pair of electrodes 3 and 5 are preferably transparent electrodes that sufficiently transmit visible light and are more preferably made of a material having high light transmittance in a visible region and high conductivity. Examples of the material for the electrodes 3 and 5 include metals and metal oxides such as indium tin oxide alloy (ITO), tin oxide (NESA), indium zinc oxide (IZO (registered trademark)), silver oxide, vanadium oxide, molybdenum oxide, gold, silver, platinum, copper, indium, and chromium; silicon materials such as polycrystalline silicon and amorphous silicon; and carbon materials such as carbon black, graphene, graphite, and glassy carbon.

The electrodes 3 and 5 are also suitably made of a conductive polymer whose conductivity is improved by doping treatment or the like (e.g., polyaniline, polypyrrole, polythiophene, polyacetylene, poly(p-phenylene), and complexes of polyethylenedioxythiophene and polystyrenesulfonic acid (PEDOT:PSS)). Since the EC device 1 according to this embodiment preferably exhibits high transmittance in a decolored state, for example, ITO, IZO, NESA, PEDOT:PSS, or graphene is particularly preferably used. They can be used in various forms such as bulk and fine particles.

These materials may be used alone or in combination of two or more. In this embodiment, both the pair of electrodes 3 and 5 are transparent electrodes. However, for example, only one of the pair of electrodes 3 and 5 may be a transparent electrode. The material for the electrodes can be appropriately selected in accordance with the applications.

EC Layer

The EC layer 7 contains an electrolyte, an organic EC material, and a solvent and is preferably obtained by dissolving an electrolyte and an organic EC material such as a low-molecular-weight organic material in a solvent.

The solvent contained in the EC layer 7 is not particularly limited as long as an electrolyte can be dissolved in the solvent, but is preferably a polar solvent. Specific examples of the solvent include water and organic polar solvents such as methanol, ethanol, propylene carbonate, ethylene carbonate, dimethyl sulfoxide, dimethoxyethane, acetonitrile, 7-butyrolactone, 7-valerolactone, sulfolane, dimethylformamide, dimethoxyethane, tetrahydrofuran, acetonitrile, propionitrile, dimethylacetamide, methylpyrrolidinone, and dioxolane.

The electrolyte may be any salt that dissociates into ions, has good solubility, and contains a cation or anion that has electron-donating properties to the degree that coloring of the organic EC material can be achieved. Examples of the electrolyte include various inorganic ion salts such as alkali metal salts and alkaline-earth metal salts, quaternary ammonium salts, and cyclic quaternary ammonium salts. Specific examples of the electrolyte include alkali metal salts of Li, Na, and K, such as $LiClO_4$, LiSCN, $LiBF_4$, $LiAsF_6$, $LiCF_3SO_3$, $LiPF_6$, LiI, NaI, NaSCN, $NaClO_4$, $NaBF_4$, $NaAsF_6$, KSCN, and KCl; quaternary ammonium salts such as $(CH_3)_4NBF_4$, $(C_2H_5)_4NBF_4$, $(n-C_4H_9)_4NBF_4$, $(C_2H_5)_4NBr$, $(C_2H_5)_4NClO_4$, and $(n-C_4H_9)_4NClO_4$; and cyclic quaternary ammonium salts. A generally known structure such as $ClO_4^-$, $CF_3SO_3^-$, $BF_4^-$, $PF_6^-$, or $(CF_3SO_2)_2N^-$ is used as anion species. An ionic liquid may also be used. These electrolyte materials may be used alone or in combination of two or more.

The EC layer 7 is preferably in the form of liquid or gel. The EC layer 7 is suitably used in the form of solution, but can also be used in the form of gel. The EC layer 7 is used in the form of gel by, for example, a method in which a gelling agent such as a polymer is added to a solution containing an electrolyte and an organic EC material or a method in which a solution containing an electrolyte and an organic EC material is supported on a network structural body (e.g., sponge) with transparency and flexibility.

In the case where a gelling agent is added to a solution containing an electrolyte and an organic EC material, the gelling agent is not particularly limited. Examples of the gelling agent include polyacrylonitrile, carboxymethyl cellulose, poly(vinyl chloride), poly(vinyl bromide), poly(ethylene oxide), poly(propylene oxide), polyurethane, polyacrylate, polymethacrylate, polyamide, polyacrylamide, polyester, polyvinylidene fluoride, and Nafion (registered trademark). As described above, the EC layer 7 may be, for example, a viscous layer or a gel layer.

The organic EC material is a material that is soluble in a solvent and can be colored and decolored through an electrochemical reaction. The organic EC material may be an organic compound represented by any one of general formulae (1) to (5) described later or a publicly known oxidation/reduction coloring organic EC material. A plurality of materials may also be used in combination. That is, the EC device 1 according to this embodiment may have a plurality of types of EC materials.

For the organic EC material, one type of cathodic material that is colored through reduction reaction may be used or a plurality of types of cathodic materials may be used. One type of anodic material that is colored through oxidation reaction may be used or a plurality of types of anodic materials may be used. Alternatively, for the organic EC material, one type of anodic material and one type of cathodic material may be used in combination or a plurality of types of anodic materials and a plurality of types of cathodic materials may be used in combination. The term "plurality of types" herein refers to a plurality of types of materials having different chemical structures. The term "different types" refers to different chemical structures. The EC device 1 according to this embodiment contains one or more types of cathodic materials. As described above, one or more types of anodic materials may be contained.

By combining the EC organic compound with another coloring material with a different color, the EC device can develop a desired color. The other coloring organic compound preferably exhibits absorption in the wavelength range of 400 nm or more and 800 nm or less and more preferably exhibits absorption in the wavelength range of 420 nm or more and 700 nm or less. By combining the EC material according to this embodiment with a plurality of other EC materials, an EC device that is colored in black through absorption of light in the entire visible region can be produced.

Herein, the anodic EC compound is a compound that is colored when losing electrons, and the cathodic EC compound is a compound that is colored when receiving electrons.

Specific examples of the organic EC material include organic dyes such as bipyridine derivatives, e.g., viologen derivatives, styryl derivatives, fluoran derivatives, cyanine derivatives, anthraquinone derivatives, and aromatic amine derivatives; and organic metal complexes such as metal-bipyridyl complexes and metal-phthalocyanine complexes. The bipyridine derivative such as a viologen derivative can be used as a cathodic material that is decolored in a dication state which is stable with a counterion and that is colored in a cation state through one-electron reduction reaction.

Examples of the anodic EC material that is colored in an oxidation state include thiophene derivatives; metallocene derivatives such as ferrocene, tetra-t-butylferrocene, and titanocene; phenazine derivatives such as 5,10-dihydro-5,10-dimethylphenazine and 5,10-dihydro-5,10-diethylphenazine; aromatic amine derivatives such as triphenylamine derivatives, phenothiazine derivatives, and phenoxazine derivatives; phenylenediamine derivatives such as pyrrole derivatives and N,N',N,N'-tetramethyl-p-phenylenediamine; and pyrazoline derivatives such as 1-phenyl-2-pyrazoline. However, the anodic EC material used in the EC device 1 according to this embodiment is not limited thereto.

Examples of the cathodic EC material that is colored in a reduction state include bipyridine derivatives such as viologen derivatives, anthraquinone derivatives, ferrocenium salt compounds, and styryl derivatives. Among them, the EC device 1 preferably contains a bipyridine derivative as a cathodic EC material.

Specific examples of the compound that is colored in a reduction state include viologen compounds such as N,N'-diheptyl bipyridinium diperchlorate, N,N'-diheptyl bipyridinium ditetrafluoroborate, N,N'-diheptyl bipyridinium dihexafluorophosphate, N,N'-diethyl bipyridinium diperchlorate, N,N'-diethyl bipyridinium ditetrafluoroborate, N,N'-diethyl bipyridinium dihexafluorophosphate, N,N'-dibenzyl bipyridinium diperchlorate, N,N'-dibenzyl bipyridinium ditetrafluoroborate, N,N'-dibenzyl bipyridinium dihexafluorophosphate, N,N'-diphenyl bipyridinium diperchlorate, N,N'-diphenyl bipyridinium ditetrafluoroborate, N,N'-diphenyl bipyridinium dihexafluorophosphate; anthraquinone compounds such as 2-ethylanthraquinone, 2-t-butylanthraquinone, and octamethylanthraquinone; ferrocenium salt compounds such as ferrocenium tetrafluoroborate and ferrocenium hexafluorophosphate; and styryl compounds.

By extracting and analyzing the compound contained in the EC layer 7 by a publicly known method, it can be confirmed whether the compound is contained in the EC device. For example, extraction is performed by chromatography and analysis is performed by NMR. When the electrochromic layer is solid, analysis can be performed by, for example, TOF-SIMS.

Hereafter, an EC organic compound that can reduce a change in absorption spectrum due to the difference in ambient temperature will be described. The EC organic compound that can reduce a change in absorption spectrum due to the difference in ambient temperature preferably has a structure represented by general formula (2) below. The organic compound represented by the general formula (2) below is a viologen derivative, which is one of bipyridine derivatives.

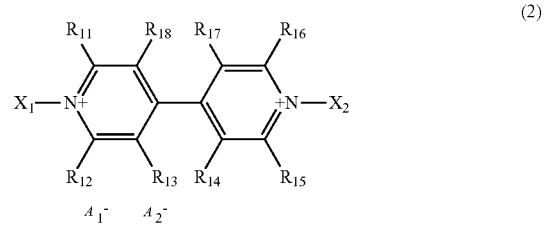

(2)

In the general formula (2), $R_{11}$ to $R_{18}$ are each independently selected from the group consisting of a hydrogen atom, an alkyl group optionally having a substituent, an alkoxy group optionally having a substituent, an aryl group optionally having a substituent, a heterocyclic group optionally having a substituent, a halogen atom, and $P(O)R_{23}$. Substituents of $R_{11}$ to $R_{18}$ may form a fused ring. Substituents of $R_{11}$ and $R_{18}$ or $R_{17}$ and $R_{18}$ form a fused ring. If $R_{18}$ represents $P(O)R_{23}$, $R_{18}$ bonds to $R_{17}$ to form a fused ring. $R_{23}$ represents an aryl group optionally having a substituent.

$X_1$ and $X_2$ are each independently selected from the group consisting of an alkyl group optionally having a substituent, an aryl group optionally having a substituent, and an aralkyl group optionally having a substituent. $A_1^-$ and $A_2^-$ each independently represent a monovalent anion.

The alkyl group represented by $R_{11}$ to $R_{18}$ and $X_1$ and $X_2$ preferably has 1 to 8 carbon atoms and may be a linear, branched, or cyclic group. A hydrogen atom in the alkyl group may be substituted with a halogen atom, an ester group, or a cyano group. When the hydrogen atom is substituted with a halogen atom, a fluorine atom is preferred. Alternatively, a carbon atom in the alkyl group may be substituted with an ester group or a cyano group.

Specific examples of the alkyl group include a methyl group, an ethyl group, a n-propyl group, an isopropyl group, a n-butyl group, a t-butyl group, an octyl group, a cyclohexyl group, and a trifluoromethyl group. The alkyl group may have a terminal adsorptive group with which the alkyl group adsorbs onto a porous electrode or an acid ester group of the adsorptive group. Specific examples of the adsorptive group or the acid ester group of the adsorptive group include a carboxy group, a carboxylate group, a sulfonic acid group, a sulfonate group, a phosphonic acid group, a phosphonate group, and a trialkoxysilyl group. Furthermore, the alkyl group may have, at its terminal, an ionic group such as pyridinium or quinolinium to improve the solubility in an organic solvent.

The alkoxy group represented by $R_{11}$ to $R_{18}$ preferably has 1 to 8 carbon atoms and may be a linear, branched, or cyclic group. Specific examples of the alkoxy group include a methoxy group, an ethoxy group, an isopropoxy group, a t-butoxy group, an octoxy group, a cyclohexyloxy group, and a trifluoromethoxy group. A hydrogen atom in the alkoxy group may be substituted with a halogen atom. When the hydrogen atom is substituted with a halogen atom, a fluorine atom is preferred.

Examples of the aryl group represented by $R_{11}$ to $R_{18}$, $X_1$ and $X_2$, and $R_{23}$ include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

When the aryl group has a substituent such as an alkyl group or an alkoxy group, the alkyl group or the alkoxy group may have a terminal adsorptive group with which the alkyl group or the alkoxy group adsorbs onto a porous electrode or an acid ester group of the adsorptive group. Specific examples of the adsorptive group or the acid ester group of the adsorptive group include a carboxy group, a carboxylate group, a sulfonic acid group, a sulfonate group, a phosphonic acid group, a phosphonate group, and a trialkoxysilyl group. Furthermore, the alkyl group or the alkoxy group that is a substituent of the aralkyl group may have, at its terminal, an ionic group such as pyridinium or quinolinium to improve the solubility in an organic solvent.

When the aryl group has a substituent, the substituent may be at least one of a halogen atom, an alkyl group having 1 to 8 carbon atoms, and an alkoxy group having 1 to 8 carbon atoms.

Examples of the heterocyclic group represented by $R_{11}$ to $R_{18}$ and optionally having a substituent include a thienyl group, a pyrrolyl group, a pyridyl group, an oxazolyl group, an oxadiazolyl group, a thiazolyl group, a thiadiazolyl group, a terthienyl group, a quinolyl group, an isoquinolyl group, and a carbazolyl group.

When the heterocyclic group has a substituent, the substituent may be at least one of an alkyl group having 1 to 8 carbon atoms and an alkoxy group having 1 to 8 carbon atoms.

Examples of the halogen atom represented by $R_{11}$ to $R_{18}$ include fluorine, chlorine, bromine, and iodine.

Examples of the aralkyl group represented by $X_1$ and $X_2$ include a benzyl group and a phenethyl group. The aralkyl group may have a substituent such as an alkyl group having 1 to 8 carbon atoms or an alkoxy group having 1 to 8 carbon atoms.

When the aralkyl group has a substituent such as an alkyl group or an alkoxy group, the alkyl group or the alkoxy group may have a terminal adsorptive group with which the alkyl group or the alkoxy group adsorbs onto a porous electrode or an acid ester group of the adsorptive group. Specific examples of the adsorptive group or the acid ester group of the adsorptive group include a carboxy group, a carboxylate group, a sulfonic acid group, a sulfonate group, a phosphonic acid group, a phosphonate group, and a trialkoxysilyl group. Furthermore, the alkyl group or the alkoxy group that is a substituent of the aralkyl group may have, at its terminal, an ionic group such as pyridinium or quinolinium to improve the solubility in an organic solvent.

$A_1^-$ and $A_2^-$ may be the same or different and are selected from anions such as $PF_6^-$, $ClO_4^-$, $BF_4^-$, $AsF_6^-$, $SbF_6^-$, $CF_3SO_3^-$, and $(CF_3SO_2)_2N^-$ and halogen anions such as $Br^-$, $Cl^-$, and $I^-$. $A_1^-$ and $A_2^-$ preferably represent $PF_6^-$, $ClO_4^-$, $BF_4^-$, $CF_3SO_3^-$, or $(CF_3SO_2)_2N^-$. $A_1^-$ and $A_2^-$ more preferably represent the same anion.

A Compound Having High Transparency.

Since the organic compound according to this embodiment has a structure represented by the general formula (2), the organic compound obtained when dissolved in a solvent include an organic compound represented by general formula (1). The organic compound represented by the general formula (1) is an organic compound in which substituents of $R_{17}$ and $R_{18}$ in the general formula (2) form a fused ring.

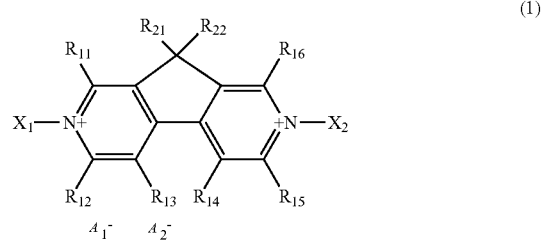

(1)

In the general formula (1), the same substituents as those in the general formula (2) are designated by the same symbols. In the general formula (1), $R_{21}$ and $R_{22}$ are each independently selected from the group consisting of a hydrogen atom, an alkyl group optionally having a substituent, an aryl group optionally having a substituent, and an aralkyl group optionally having a substituent.

Each of the alkyl groups represented by $X_1$, $X_2$, $R_{11}$ to $R_{16}$, and $R_{21}$ and $R_{22}$ preferably has 1 to 8 carbon atoms and may be a linear, branched, or cyclic group. A hydrogen atom in the alkyl group may be substituted with a halogen atom, an ester group, or a cyano group. When the hydrogen atom is substituted with a halogen atom, a fluorine atom is preferred. Alternatively, a carbon atom in the alkyl group may be substituted with an ester group or a cyano group.

Specific examples of the alkyl group include a methyl group, an ethyl group, a n-propyl group, an isopropyl group, a n-butyl group, a t-butyl group, an octyl group, a cyclohexyl group, and a trifluoromethyl group.

The alkyl group may have a terminal adsorptive group with which the alkyl group adsorbs onto a porous electrode or an acid ester group of the adsorptive group. Specific examples of the adsorptive group or the acid ester group of the adsorptive group include a carboxy group, a carboxylate group, a sulfonic acid group, a sulfonate group, a phosphonic acid group, a phosphonate group, and a trialkoxysilyl group.

Furthermore, the alkyl group may have, at its terminal, an ionic group such as pyridinium or quinolinium to improve the solubility in an organic solvent.

Examples of the aryl group represented by $X_1$, $X_2$, $R_{11}$ to $R_{16}$, and $R_{21}$ and $R_{22}$ and optionally having a substituent include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group.

When the aryl group has a substituent, the substituent may be at least one of a halogen atom, an alkyl group having 1 to 8 carbon atoms, and an alkoxy group having 1 to 8 carbon atoms. When the aryl group has a substituent such as an alkyl group or an alkoxy group, the alkyl group or the alkoxy group may have a terminal adsorptive group with which the alkyl group or the alkoxy group adsorbs onto a porous electrode or an acid ester group of the adsorptive group. Specific examples of the adsorptive group or the acid ester group of the adsorptive group include a carboxy group, a carboxylate group, a sulfonic acid group, a sulfonate group, a phosphonic acid group, a phosphonate group, and a trialkoxysilyl group. Furthermore, the alkyl group or the alkoxy group that is a substituent of the aralkyl group may have, at its terminal, an ionic group such as pyridinium or quinolinium to improve the solubility in an organic solvent.

Examples of the aralkyl group represented by $X_1$, $X_2$, $R_{21}$, and $R_{22}$ and optionally having a substituent include a benzyl group and a phenethyl group. The aralkyl group may have a substituent such as an alkyl group having 1 to 8 carbon atoms or an alkoxy group having 1 to 8 carbon atoms.

When the aralkyl group has a substituent such as an alkyl group or an alkoxy group, the alkyl group or the alkoxy group may have a terminal adsorptive group with which the alkyl group or the alkoxy group adsorbs onto a porous electrode or an acid ester group of the adsorptive group. Specific examples of the adsorptive group or the acid ester group of the adsorptive group include a carboxy group, a carboxylate group, a sulfonic acid group, a sulfonate group, a phosphonic acid group, a phosphonate group, and a trialkoxysilyl group. Furthermore, the alkyl group or the alkoxy group that is a substituent of the aralkyl group may have, at its terminal, an ionic group such as pyridinium or quinolinium to improve the solubility in an organic solvent.

The method for producing the organic compound represented by the general formula (1) is not particularly limited. For example, the organic compound can be produced by the following method. In the case where $X_1$ and $X_2$ represent an alkyl group or an aralkyl group, the compound represented by the general formula (1) can be produced by reacting an organic compound represented by general formula (6) and a halide in a particular solvent and then performing, in a particular solvent, an anion exchange reaction with a salt containing a desired anion. In the case where $X_1$ and $X_2$ represent an aryl group, first, 2,4-dinitrophenyl-2,7'-diazafluorenium is synthesized through a reaction with a 2,4-dinitrophenyl halide. Then, a reaction with an aryl amine is performed and an anion exchange reaction is performed with a salt containing an anion in a particular solvent to obtain the compound represented by the general formula (1). An imine on only one side can be caused to react by selecting a solvent and a reaction temperature. By repeatedly performing the reaction, different substituents can be introduced to two imines.

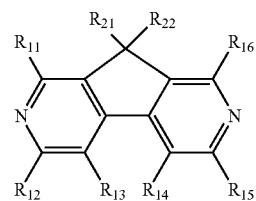

(6)

The method for producing the organic compound represented by the above general formula (6) is not particularly limited. For example, the organic compound can be produced by the following method.

In the synthesis route, $R_{11}$ to $R_{16}$ and $R_{21}$ and $R_{22}$ represent the same substituents as those in the general formula (1), and X represents a halogen atom.

An intermediate 1 can be synthesized with reference to Angew. Chem. Int. Ed. 2007, 46, 198.

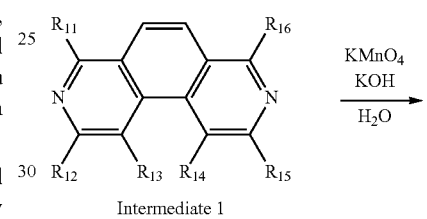

Intermediate 1

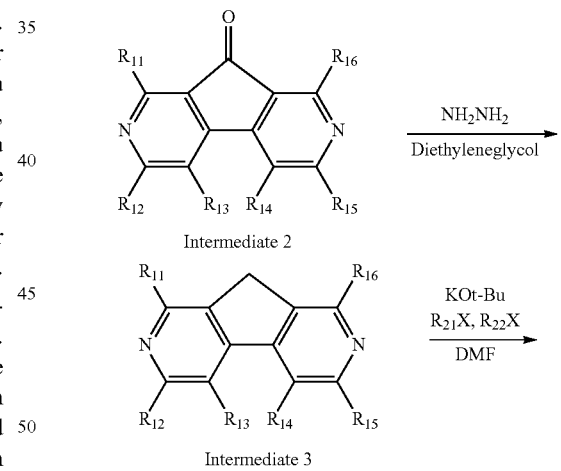

Intermediate 2

Intermediate 3

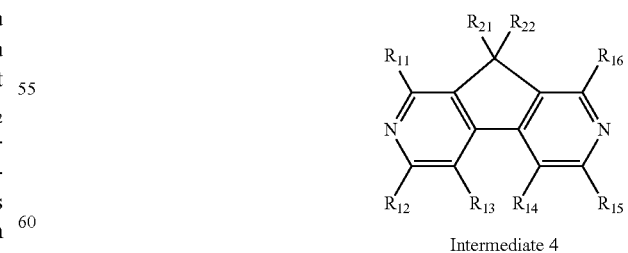

Intermediate 4

The specific structural formulae of the organic compound represented by the general formula (1) will be shown below by example. Note that the compound according to this embodiment is not limited thereto.

-continued
A-19
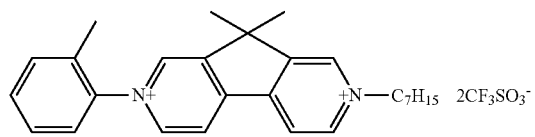 2CF₃SO₃⁻
A-20
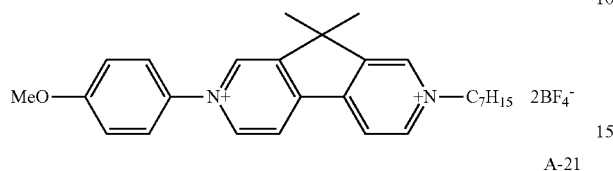 2BF₄⁻
A-21
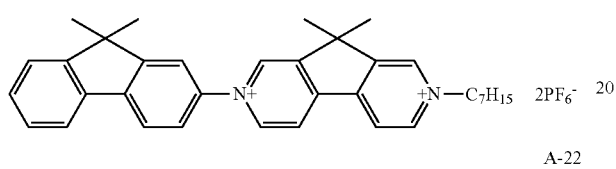 2PF₆⁻
A-22
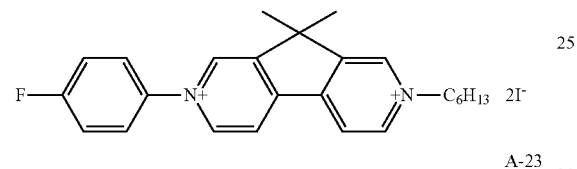 2I⁻
A-23
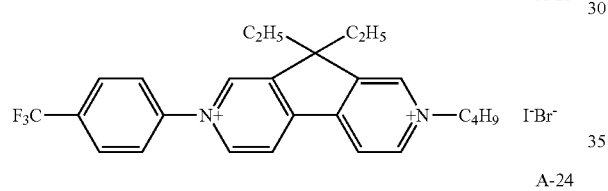 I⁻Br⁻
A-24
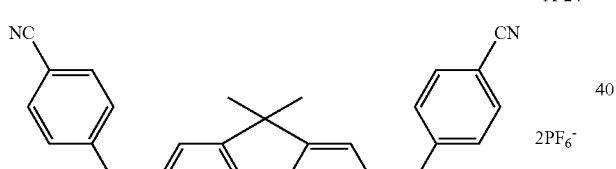 2PF₆⁻
A-25
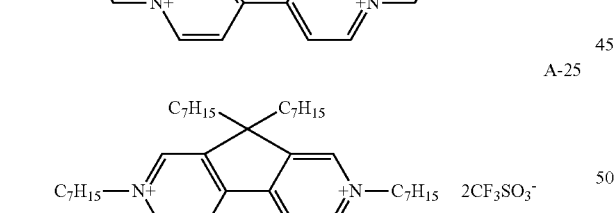 2CF₃SO₃⁻
A-26
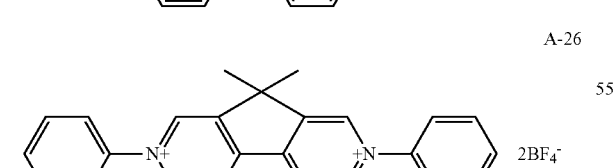 2BF₄⁻
A-27
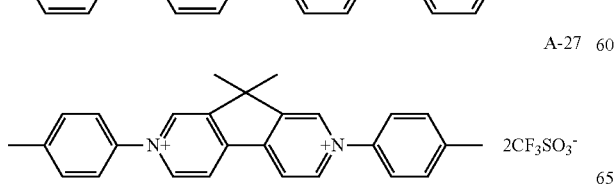 2CF₃SO₃⁻
A-28
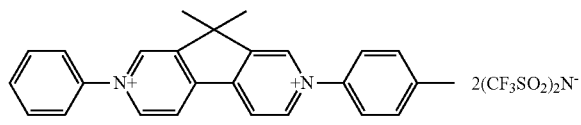 2(CF₃SO₂)₂N⁻
A-29
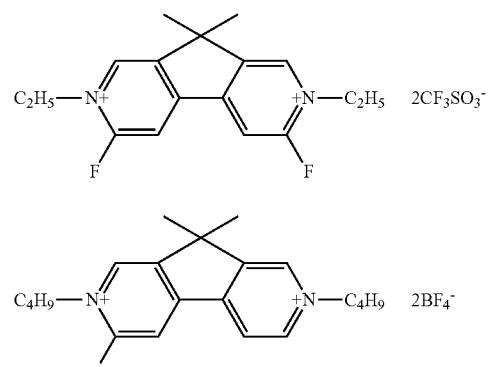 2CF₃SO₃⁻
A-30
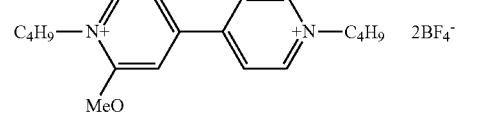 2BF₄⁻
A-31
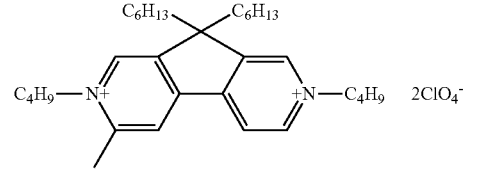 2ClO₄⁻
A-32
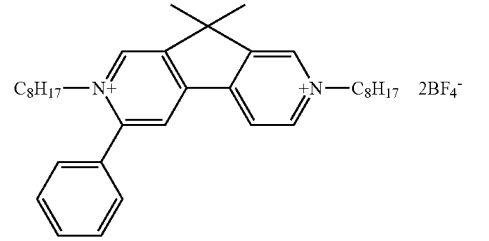 2BF₄⁻
A-33
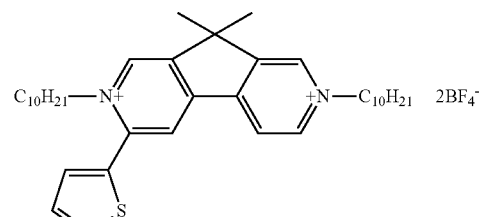 2BF₄⁻
A-34
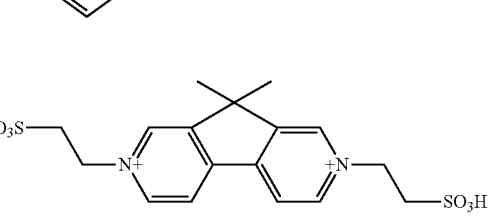 2Br⁻
A-35
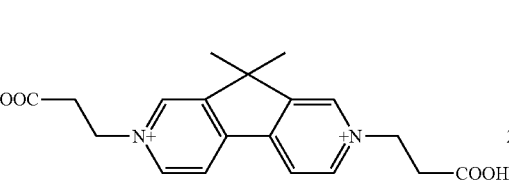 2Br⁻

-continued

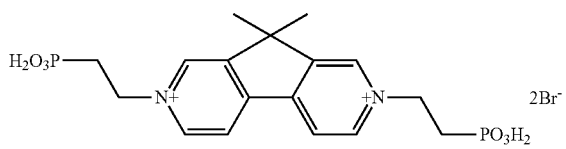
A-36

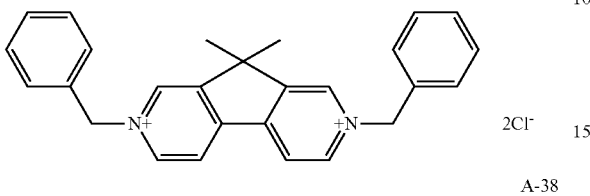
A-37

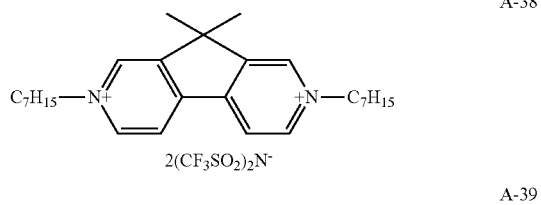
A-38

A-39

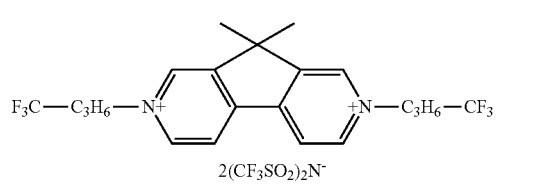
A-40

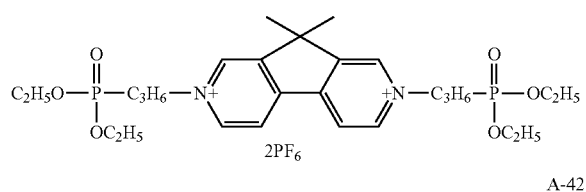
A-41

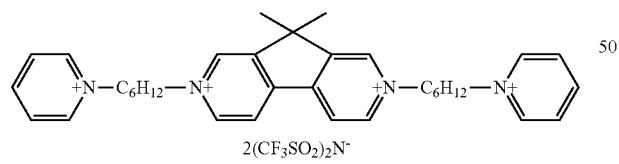
A-42

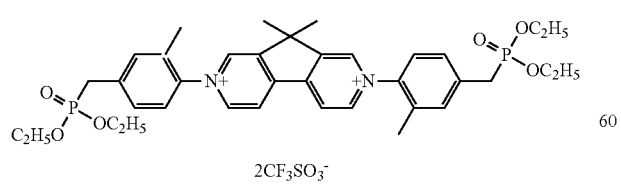
A-43

The organic compound represented by the general formula (2) includes an organic compound represented by general formula (3). The organic compound represented by the general formula (3) is an organic compound in which substituents of $R_{11}$ and $R_{18}$ in the general formula (2) form a fused ring.

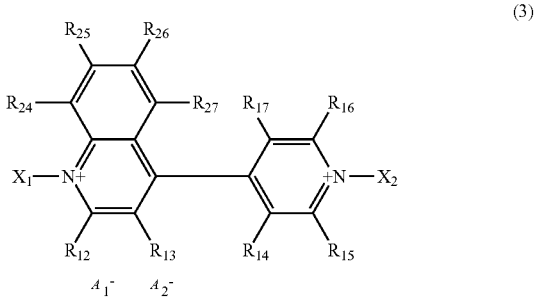
(3)

Herein, in the general formula (3), the same substituents as those in the general formula (2) are designated by the same symbols. In the general formula (3), $R_{24}$ to $R_{27}$ are each independently selected from the same substituents as those in $R_{11}$ to $R_{18}$. Note that substituents of $R_{16}$ and $R_{17}$ may form a fused ring.

The method for producing the organic compound represented by the general formula (3) is not particularly limited. For example, the organic compound can be produced by the following method. In the case where $X_1$ and $X_2$ represent an alkyl group or an aralkyl group in the general formula (3), the organic compound can be produced by reacting a corresponding diimine derivative (2,7-diazafluorene, 4-pyridyl-(4-quinoline), or 4,4'-biquinoline) and a halide in a particular solvent and then performing, in a particular solvent, an anion exchange reaction with a salt containing a desired anion.

In the case where $X_1$ and $X_2$ represent an aryl group, a 2,4-dinitrophenyl-yl-diimine derivative is synthesized through a reaction with a 2,4-dinitrophenyl halide. Then, a reaction with an aryl amine is performed and an anion exchange reaction is performed with a salt containing an anion in a particular solvent. An imine on only one side can be caused to react by selecting a solvent and a reaction temperature. By repeatedly performing the reaction, different substituents can be introduced to two imines.

The specific structural formulae of the organic compound represented by the general formula (3) will be shown below by example. Note that the compound according to this embodiment is not limited thereto.

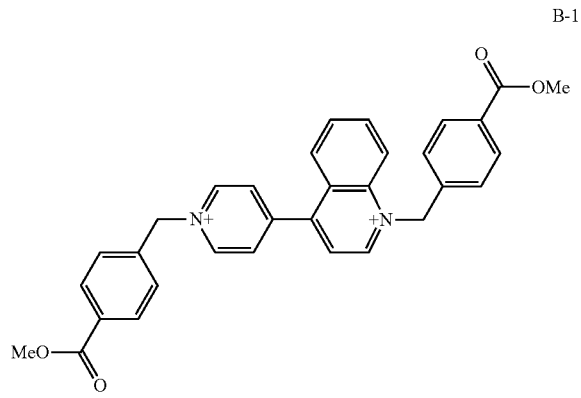
B-1

B-2

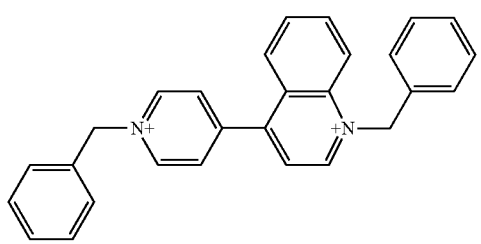

2(CF₃SO₂)₂N⁻

B-3

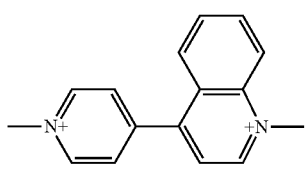

2CF₃SO₃⁻

B-4

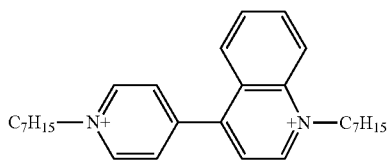

2BF₄⁻

B-5

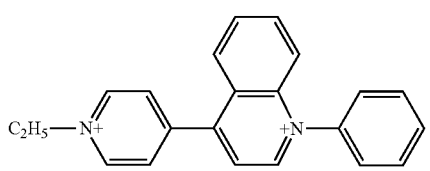

2ClO₄⁻

B-6

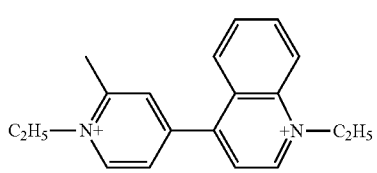

2CF₃SO₃⁻

B-7

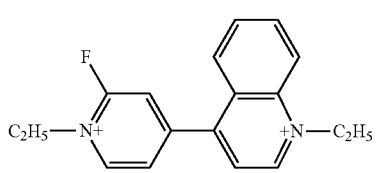

2CF₃SO₃⁻

B-8

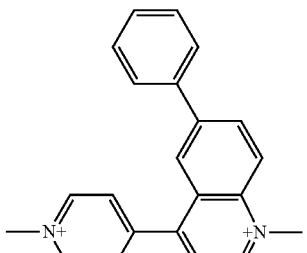

2(CF₃SO₂)₂N⁻

B-9

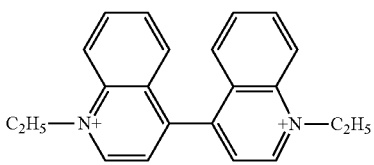

2CF₃SO₃⁻

B-10

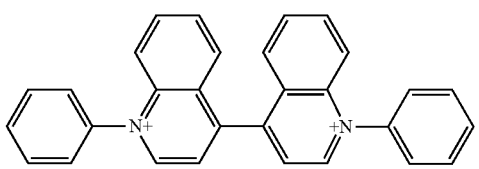

2BF₄⁻

The organic compound represented by the general formula (2) includes an organic compound represented by general formula (4). The organic compound represented by the general formula (4) is an organic compound in which substituents of $R_{17}$ and $R_{18}$ in the general formula (2) form a fused ring. Specifically, $R_{18}$ representing $P(O)R_{23}$ bonds to $R_{17}$ to form a fused ring.

$$\text{(4)}$$

Herein, in the general formula (4), the same substituents as those in the general formula (2) are designated by the same symbols.

The method for producing the organic compound represented by the general formula (4) is not particularly limited. For example, the organic compound can be synthesized with reference to Non Patent Literature such as Angew. Chem. Int. Ed. 2011, 50, 7948 or J. Am. Chem. Soc. 2015, 137, 3366.

The specific structural formulae of the organic compound represented by the general formula (4) will be shown below by example. Note that the compound according to this embodiment is not limited thereto.

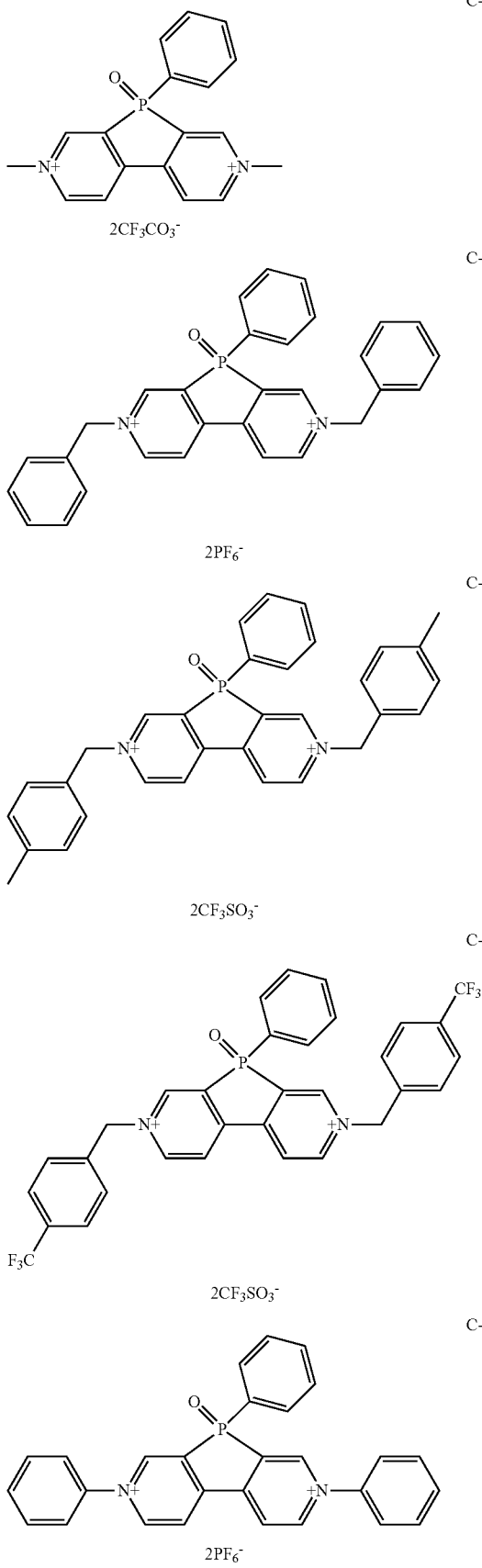

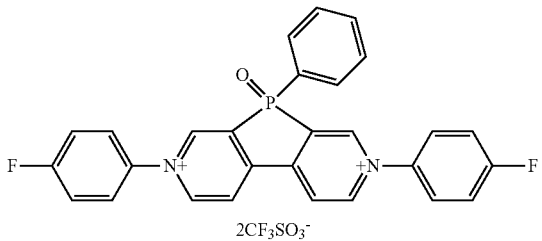

In addition to the organic compound that is represented by the general formula (2) and has a 4,4'-bipyridine skeleton, for example, an organic compound that is represented by general formula (5) and has a 2,2'-bipyridine skeleton may be contained as a cathodic EC material.

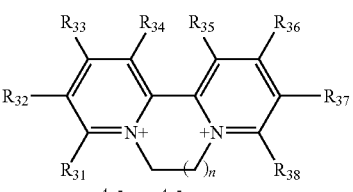

In the general formula (5), $R_{31}$ to $R_{38}$ each independently represent a hydrogen atom, an alkyl group optionally having a substituent, or an aryl group optionally having a substituent; substituents of $R_{31}$ to $R_{38}$ may form a fused ring; n represents an integer of 1 or 2; and $A_3^-$ and $A_4^-$ each independently represent a monovalent anion.

The alkyl group represented by $R_{31}$ to $R_{38}$ and optionally having a substituent preferably has 1 to 8 carbon atoms and may be a linear, branched, or cyclic group. The hydrogen atom may be substituted with a fluorine atom. Alternatively, a carbon atom in the alkyl group may be substituted with an ester group or a cyano group.

Specific examples of the alkyl group include a methyl group, an ethyl group, a n-propyl group, an isopropyl group, a n-butyl group, a t-butyl group, an octyl group, a cyclohexyl group, and a trifluoromethyl group. The alkyl group may have a terminal adsorptive group with which the alkyl group adsorbs onto a porous electrode. Specific examples of the adsorptive group include a carboxy group, a sulfonic acid group, a phosphonic acid group, a phosphoric acid group, and a trialkoxysilyl group.

Examples of the aryl group represented by $R_{31}$ to $R_{38}$ and optionally having a substituent include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group. When the aryl group has a substituent, the substituent may be at least one of a halogen atom, an alkyl group having 1 to 8 carbon atoms, and an alkoxy group having 1 to 8 carbon atoms.

$A_3^-$ and $A_4^-$—may be the same or different and are selected from anions such as $PF_6^-$, $ClO_4^-$, $BF_4^-$, $AsF_6^-$, $SbF_6^-$, $CF_3SO_3^-$, and $(CF_3SO_2)_2N^-$ and halogen anions such as $Br^-$, $Cl^-$, and $I^-$. $A_3^-$ and $A_4^-$ preferably represent $PF_6^-$, $ClO_4^-$, $BF_4^-$, $CF_3SO_3^-$, or $(CF_3SO_2)_2N^-$. $A_3^-$ and $A_4^-$ more preferably represent the same anion.

The method for producing the organic compound represented by the general formula (5) is not particularly limited. For example, the organic compound can be produced by reacting a 2,2'-bipyridine derivative or a 1,10-phenanthroline derivative with dibromoethane or dibromopropane and then performing, in a particular solvent, an anion exchange reaction with a salt containing a desired anion.

The specific structural formulae of the organic compound represented by the general formula (5) will be shown below by example. Note that the compound according to this embodiment is not limited thereto.

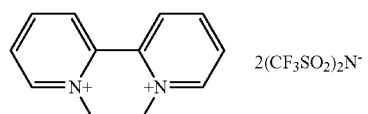
D-1

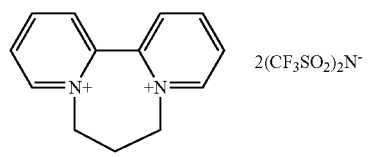
D-2

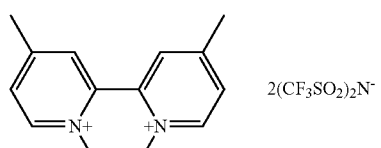
D-3

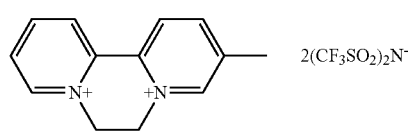
D-4

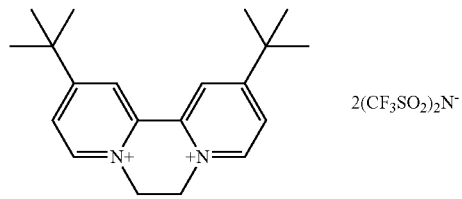
D-5

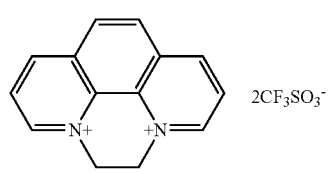
D-6

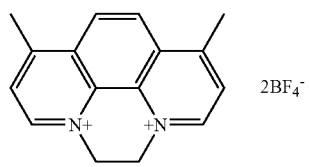
D-7

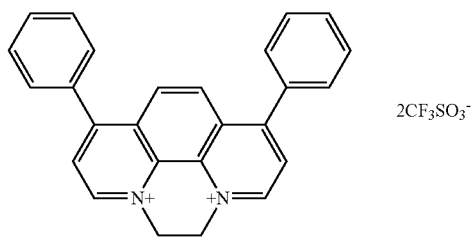
D-8

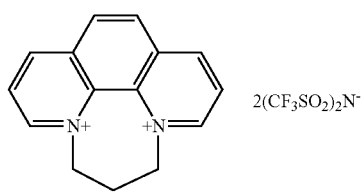
D-9

When the EC layer 7 contains another EC organic compound in addition to any one of the organic compounds represented by the general formulae (1) to (5), the other EC organic compound is preferably a phenazine compound, a ferrocene compound, a metallocene compound, a phenylenediamine compound, or a pyrazoline compound. The organic compounds according to this embodiment represented by the general formulae (1) to (5) may be further contained as the other EC organic compound.

Spectral Characteristics

The EC device 1 according to this embodiment satisfies formula (1) and preferably satisfies formula (2) in the wavelength range of 450 nm or more and 650 nm or less.

Herein, the absorbance f1(m) is a value obtained by normalizing the absorbance of an EC layer 7 in a colored state at an ambient temperature of 0° C. at any wavelength m in the range of 450 nm or more and 650 nm or less with respect to the absorbance at a wavelength n at which a bipyridine derivative exhibits radical absorption. The absorbance f2(m) is a value obtained by normalizing the absorbance of an EC layer 7 in a colored state at an ambient temperature of 80° C. at the wavelength m with respect to the absorbance at the wavelength n. The absorbances f1(m) and f2(m) can each be a value at any wavelength m in a spectrum obtained by normalizing the absorption spectrum of the EC layer 7 colored as a result of driving of the EC device 1 with respect to the absorbance at the wavelength n. The absorbances f1(m) and f2(m) may also each be a value obtained by normalizing the absorbance at any wavelength m with respect to the absorbance at the wavelength n.

$$0.6 < f2(m)/f1(m) < 1.4 \quad (1)$$

$$0.8 < f2(m)/f1(m) < 1.2 \quad (2)$$

The absorbance ratio f2(m)/f1(m) refers to a difference in the absorbance of the EC layer 7 at different ambient temperatures. When the absorbance ratio f2(m)/f1(m) is 1, the intensity ratio is constant regardless of the ambient temperature. The deviation of the absorbance ratio f2(m)/f1(m) from 1 increases a change in the shape of the absorption spectrum of the EC device due to the ambient temperature.

In this specification, the "ambient temperature" generally refers to a temperature of the EC device itself. More specifically, the "ambient temperature" refers to a temperature of the substrate surface of the EC device during the measurement of absorption spectrum, the temperature being measured with a thermocouple or a thermal radiometer. The absorbances f1(m) and f2(m) are absorbances obtained when the ambient temperatures are 0° C. and 80° C., respectively. Alternatively, the "ambient temperature" refers to a temperature at which the EC device is left to stand in a temperature-controlled chamber such as a constant temperature oven for a sufficiently long time and thus the temperature of the EC device reaches an equilibrium state. The absorbances f1(m) and f2(m) are absorbances obtained when the ambient temperatures are 0° C. and 80° C., respectively.

The EC device 1 according to this embodiment that satisfies the formula (1) has only a small change in the absorption spectrum in a colored state due to the ambient temperature. Therefore, the change in the absorption spectrum due to an ambient temperature at which the EC device 1 is driven can be reduced compared with the related art.

It is sufficient that the produced EC device 1 has temperature characteristics that satisfy the formula (1) and preferably satisfy the formula (2). However, it is desirable that the organic compound that satisfies the formula (1) and preferably satisfies the formula (2) be used for the EC layer 7.

The organic compounds according to this embodiment represented by the general formulae (1) to (5) are EC compounds that are colored in a reduction state. The EC compounds have only a small change in color in a colored state of the EC compounds due to the operating temperature, that is, the ambient temperature. In other words, even if the temperature changes, the organic compounds according to this embodiment have no change or only a small change in a wavelength at which the transmittance is decreased in a reduction state.

It is believed that a change in the wavelength of radical absorption due to temperature change is caused by association of radical molecules. That is, it is believed that $\pi$-$\pi$ stacking of aromatic sites of radical molecules considerably contributes to the change. If the materials form an associate, the absorption of monomers and the absorption of associates are superimposed in the absorption spectrum. Since ease of formation of associates is dependent on the temperature, the ratio of the absorption of monomers and the absorption of associates changes with the ambient temperature.

As a result of studies conducted by the present inventors, they have found that the bipyridine derivatives represented by the general formulae (1) to (5) do not easily form an associate even if the ambient temperature changes and thus the form of monomer is relatively easily maintained. In the organic compound represented by the general formula (2), adjacent substituents such as $R_{11}$ and $R_{18}$ or $R_{17}$ and $R_{18}$ bond to each other to form a fused ring, and such a structure contributes to suppressing the formation of an associate of the bipyridine derivative.

In other words, since the organic compounds represented by the general formulae (1) to (5) have lower molecular symmetry than bipyridinium and known viologen derivatives, the occurrence of association is believed to be suppressed compared with the related art. Specifically, for example, in the bipyridine derivative represented by the general formula (1), the substituents $R_{21}$ and $R_{22}$ project in a vertical direction with respect to the aromatic site of a radical molecule and thus the occurrence of association is believed to be further suppressed. Therefore, the substituents $R_{21}$ and $R_{22}$ more preferably represent an alkyl group, an aryl group, or an aralkyl group.

In this specification, the phrase "have only a small change in color in a colored state" is desirably a state that satisfies the formula (1) or the formula (2). Furthermore, the maximum absorption wavelength of an organic compound colored in a reduction state desirably does not change at 0° C. and 80° C. If the maximum wavelength does not change, the change in color of radical absorption is small. However, if another maximum wavelength is observed or the maximum wavelength is shifted, the change in color of radical absorption is large.

In the EC device 1 according to this embodiment, as described above, the change in the absorption spectrum of the EC device due to a change in the ambient temperature at which the EC device is driven can be reduced compared with the related art by using, as an EC compound, an organic compound having only a small change in absorption spectrum due to the change in the ambient temperature. That is, according to the EC device 1, the change in absorption spectrum in a colored state due to a change in the ambient temperature can be reduced, which can reduce a change in color when the EC device 1 is driven. In other words, according to the EC device 1, an EC device whose temperature dependence is small can be provided.

Second Embodiment

Figure 2:
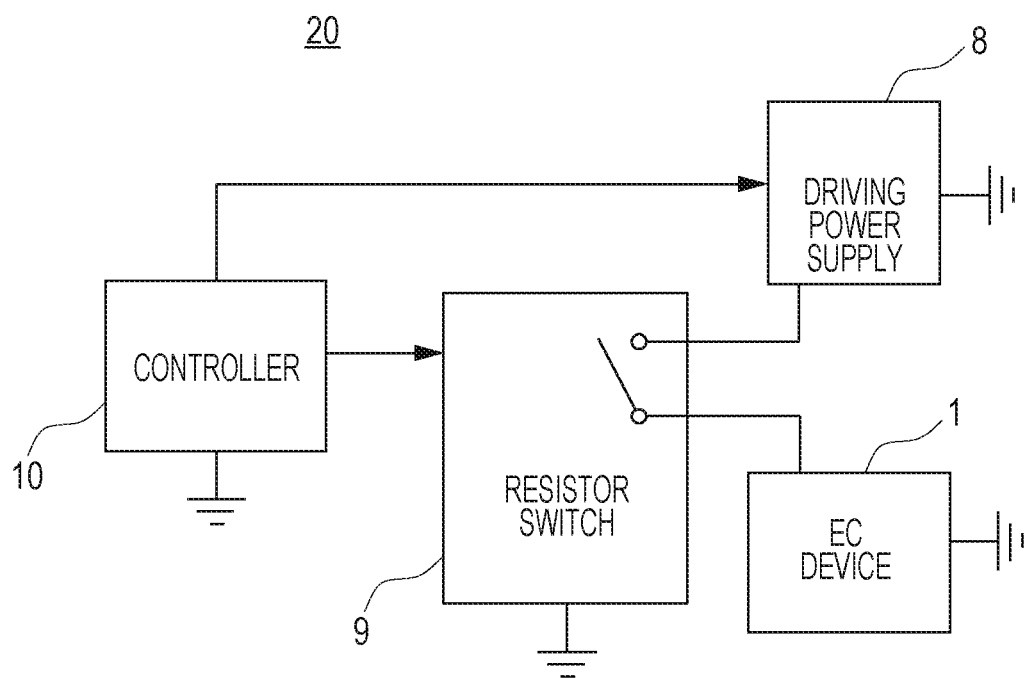
FIG. 2 schematically illustrates a configuration of an electrochromic apparatus according to a second embodiment.

FIG. 2 schematically illustrates an example of a configuration of an electrochromic apparatus 20 (hereafter referred to as an "EC apparatus 20") according to this embodiment. The EC apparatus 20 according to this embodiment includes the EC device 1 according to the first embodiment and driving means for driving the EC device 1.

The driving means is means for controlling the transmittance of the EC device 1 using pulse width modulation and includes a driving power supply 8, a resistor switch 9, and a controller 10. The driving means is configured to maintain the transmittance of the EC device without changing the peak value of a pulse voltage waveform and control the transmittance of the EC device 1 by changing the ratio (duty ratio) of the duration of voltage applied relative to a single period of the pulse voltage waveform.

The driving power supply 8 is configured to apply a voltage (driving voltage V1) required to cause an electrochemical reaction of an EC material to the EC device 1. When the EC layer 7 contains a plurality of EC materials as in the case of the EC device 1 according to this embodiment, the absorption spectrum sometimes changes because of difference in oxidation-reduction potential between the EC materials or difference in molar absorption coefficient between the EC materials. Therefore, the driving voltage V1 is preferably constant. The start of voltage application and the holding of voltage applied in the driving power supply 8 is conducted in response to the signals from the controller 10. In this embodiment, a constant voltage is applied while the light transmittance of the EC device 1 is controlled.

The resistor switch 9 is configured to interchangeably connect, in series, a resistor R1 or a resistor R2 having higher resistance than the resistor R1 in a closed circuit including the driving power supply 8 and the EC device 1. The resistance of the resistor R1 is preferably at least smaller than the highest impedance in the closed circuit of the device, preferably 10Ω or less. The resistance of the resistor R2 is preferably larger than the highest impedance in the closed circuit of the device, preferably 1 MΩ or more. The resistor R2 may be air. In this case, the closed circuit is an open circuit in a strict sense. However, this circuit can be considered to be a closed circuit when air is regarded as the resistor R2.

The controller 10 is configured to transmit switching signals to the resistor switch 9 to control switching of the resistor R1 and the resistor R2. When the resistor R1 is connected, a coloring reaction occurs in the EC device. When the resistor R2 is connected, a coloring reaction does not occur in the EC device. While the resistor R2 is connected, the EC material undergoes self-decoloration. This self-decoloration phenomenon occurs because of, for example, the instability of radical species of EC materials generated through the coloring reaction, the diffusion of the radical species into a counter electrode having a different potential, and the collision of the radical species of an anode material and the radical species of a cathode material in a solution.

The absorbance is maintained when the coloring amount and the self-decoloration amount are in balance. When the organic EC device is driven at a constant voltage from the driving power supply without changing the duty ratio, the change in absorbance is saturated via a transient state and the saturated absorbance is maintained. To decrease the absorbance, it is sufficient that the duty ratio is set to a duty ratio smaller than the immediately previous duty ratio. To increase the absorbance, it is sufficient that the duty ratio is set to a duty ratio larger than the immediately previous duty ratio. Herein, when one period of control signals is long, an increase or decrease in absorbance may be visually observed. Therefore, one period is preferably 100 milliseconds or less and more preferably 10 milliseconds or less.

The above-described driving method is merely one embodiment. For example, a method in which the peak value of voltage is changed, a method in which the erasing voltage is applied when the resistor R2 is connected, or a method in which a short-circuit is caused when the resistor R is connected can be appropriately employed.

The EC apparatus 20 according to this embodiment includes the EC device 1 according to the first embodiment that satisfies the formula (1) or the formula (2). Therefore, in the EC apparatus 20 according to this embodiment, the change in absorption spectrum due to the change in the ambient temperature at which the EC apparatus 20 is driven can be reduced compared with the related art. That is, an EC apparatus whose temperature dependence is low can be provided.

Third Embodiment

In this embodiment, the case where the EC device 1 according to the first embodiment is used as an optical filter. The optical filter according to this embodiment includes the EC device 1 according to the first embodiment. The optical filter according to this embodiment preferably includes driving means for driving the EC device. For example, the EC apparatus according to the second embodiment can be used as an optical filter and peripheral devices may be further included.

The optical filter according to this embodiment also includes an active device connected to the EC device. The active device is configured to drive the EC device 1 to control the amount of light that passes through the EC device 1. Examples of the active device include transistors and MIM devices. The transistor may include an oxide semiconductor such as InGaZnO in an active region. The active device may be directly connected to the EC device 1 or may be indirectly connected to the EC device 1 via another device.

The optical filter may be used for image pickup apparatuses such as cameras. When the optical filter is used for image pickup apparatuses, the optical filter may be disposed on a main body of an image pickup apparatus or a lens unit. Hereafter, the case where the optical filter is used as a neutral density (ND) filter will be described.

The neutral density filter is subjected to black absorption and therefore flat absorption is required across the entire visible region. The organic EC material exhibits absorption peaks in the visible region. To achieve black absorption using the organic EC material, the absorption is preferably designed so that flat absorption is achieved in the visible region and black absorption is achieved as a result of the sum of absorption of each EC material by mixing a plurality of materials having different absorption regions in the visible region. The absorption spectrum of a mixture of the organic EC materials is expressed as the sum of absorption spectra of the materials. Therefore, the black absorption can be achieved by selecting a plurality of materials having appropriate wavelength ranges and controlling the concentrations of the materials.

In general, one low-molecular-weight organic EC material can cover a wavelength range of 100 nm to 200 nm. To cover the entire visible region of 380 nm to 750 nm, at least three organic EC materials are preferably used. For example, three or more anode EC materials, three or more cathode EC materials, or two or more anode EC materials and two or more cathode EC materials are preferably used as the organic EC materials.

A driving example of the case where the optical filter according to this embodiment is used as a neutral density (ND) filter will be described. In general, the neutral density (ND) filter controls the amount of light to $½^n$ (n: integer). In the case of ½, the transmittance decreases from 100% to 50%. In the case of ¼, the transmittance decreases from 100% to 25%. When the transmittance is multiplied by ½, the amount of change in absorbance is 0.3 from the relationship $-\mathrm{LOG}(\mathrm{transmittance})=(\mathrm{absorbance})$. When the transmittance is multiplied by ¼, the amount of change in absorbance is 0.6. Therefore, for example, to reduce the amount of light from ½ to 1/64, the amount of change in absorbance is controlled from 0 to 1.8 in increments of 0.3.

When the EC layer is in the form of solution, the coloring amount may change because of fluctuation. Therefore, an external monitor for measuring the amount of light may be provided to perform more precise control.

The optical filter according to this embodiment includes the EC device 1 according to the first embodiment that satisfies the formula (1) or the formula (2). Therefore, in the optical filter according to this embodiment, the change in absorption spectrum due to the change in the ambient temperature at which the EC device is driven can be reduced compared with the related art. That is, an optical filter whose temperature dependence is low can be provided.

Furthermore, by using, as a light-controlling member, the optical filter including an organic EC device as in this embodiment, the amount of light controlled can be appropriately changed with a single filter, which advantageously decreases the number of parts and saves space.

Fourth Embodiment

Figure 4A:
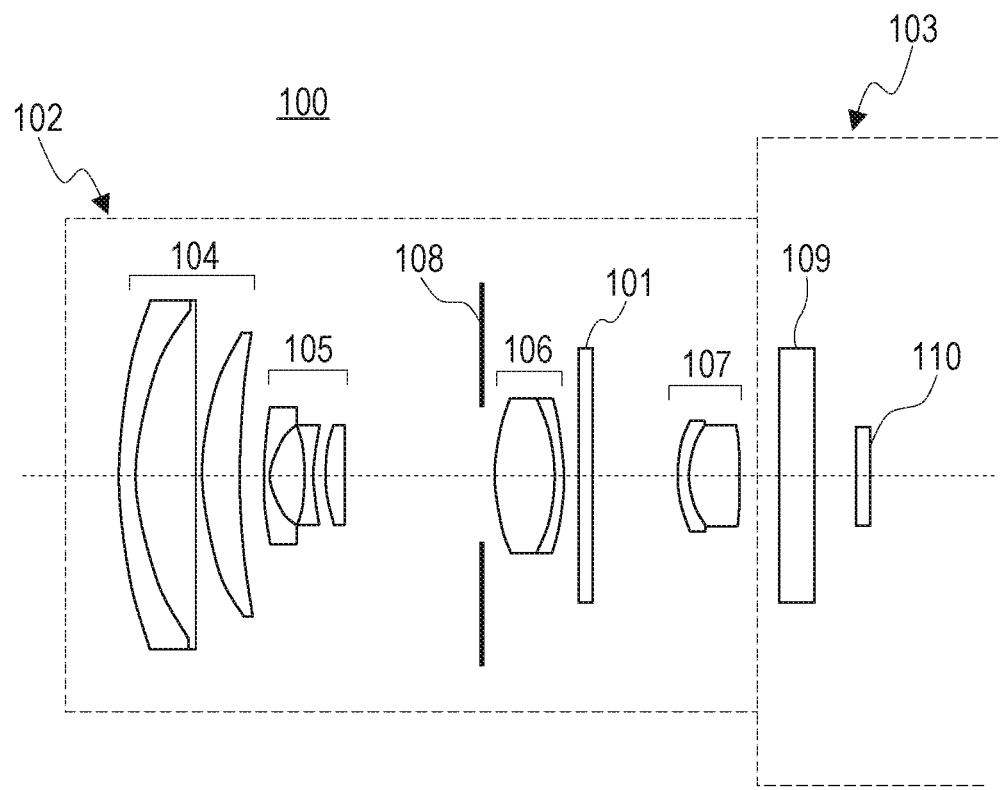
FIGS. 4A and 4B schematically illustrate examples of a structure of an image pickup apparatus according to a fourth embodiment.

In this embodiment, an image pickup apparatus 100 including the EC device 1 according to the first embodiment will be described with reference to FIG. 4A. FIG. 4A schematically illustrates an example of a structure of an image pickup apparatus 100 according to this embodiment.

The image pickup apparatus 100 is an image pickup apparatus including a lens unit 102 and an image pickup unit 103. The image pickup apparatus according to this embodiment is, for example, a digital camera or a digital video camera. An optical filter included in the image pickup apparatus according to this embodiment may be disposed immediately in front of an image pickup element. The phrase "immediately in front of an image pickup element" means that there is no member disposed between the image pickup element and the optical filter. When the image pickup apparatus includes a lens, an optical filter may be disposed on the outer side of the lens. The phrase "an optical filter is disposed on the outer side of the lens" means that an optical filter is disposed such that a lens is disposed between the optical filter and the image pickup element. When the image pickup apparatus includes a plurality of lenses, an optical filter may be disposed between the lenses.

The lens unit 102 is a rear-focusing zoom lens, and focusing is performed after the diaphragm. The lens unit 102 includes an optical filter 101 and an image pickup optical system including a plurality of lenses or lens groups. The optical filter 101 is the optical filter according to the third embodiment. The optical filter 101 may be disposed such that light having passed through the optical filter 101 passes through the image pickup optical system or such that light having passed through the image pickup optical system passes through the optical filter. The optical filter 101 may be disposed on the image pickup element side relative to the lens or on the object side relative to the lens. The lens unit 102 is detachably connected to the image pickup unit 103 via a mount member (not illustrated).

The lens unit 102 includes the optical filter 101 and four lens groups constituted by a first lens group 104 having a positive refractive power, a second lens group 105 having a negative refractive power, a third lens group 106 having a positive refractive power, and a fourth lens group 107 having a positive refractive power disposed in this order from the subject (object). The distance between the second lens group 105 and the third lens group 106 is changed for varying the magnification. The movement of part of the fourth lens group 107 brings the subject into focus. The lens unit 102 includes, for example, an aperture stop 108 between the second lens group 105 and the third lens group 106 and the optical filter 101 between the third lens group 106 and the fourth lens group 107. Light passing through the lens unit 102 passes through each of the lens groups 104 to 107, the aperture stop 108, and the optical filter 101. The amount of light can be controlled by using the aperture stop 108 and the optical filter 101.

The image pickup unit 103 includes a glass block 109 and a light-receiving element (image pickup element) 110.

The glass block 109 is a glass block such as a low-pass filter, a phase plate, or a color filter.

The light-receiving element 110 is a sensing section configured to receive light that has passed through the lens unit 102 and can be an image pickup element such as a CCD or a CMOS. The light-receiving element 110 may be a photosensor such as a photodiode. An element configured to acquire and output information on the intensity or wavelength of light can be optionally used.

In this embodiment, the optical filter 101 is disposed between the third lens group 106 and the fourth lens group 107 in the lens unit 102, but the image pickup apparatus 100 is not limited to this structure. For example, the optical filter 101 may be disposed in front of (on the subject side of) or behind (on the image pickup unit 103 side of) the aperture stop 108. Alternatively, the optical filter 101 may be disposed in front of or behind any of the first to fourth lens groups 104 to 107 or may be disposed between the lens groups. When the optical filter 101 is disposed at a position of convergence, the area of the optical filter 101 can be decreased.

The structure of the lens unit 102 is also not limited to the above structure. For example, instead of the rear-focusing system, an inner-focusing system in which focusing is performed before the diaphragm or another system may be employed. Instead of the zoom lens, a special lens such as a fisheye lens or a macro lens can be optionally selected.

Furthermore, in this embodiment, the EC device 1 of the optical filter 101 according to the third embodiment and a driving device are disposed inside the lens unit 102. However, the image pickup apparatus 100 according to this embodiment is not limited thereto. The EC device 1 of the optical filter 101 may be present inside the lens unit and the driving device for the EC device may be disposed outside the lens unit 102, that is, in the image pickup unit 103. When the driving device is disposed outside the lens unit 102, the EC device 1 inside the lens unit 102 and the driving means outside the lens unit 102 are connected to each other through wiring to control the driving.

Figure 4B:
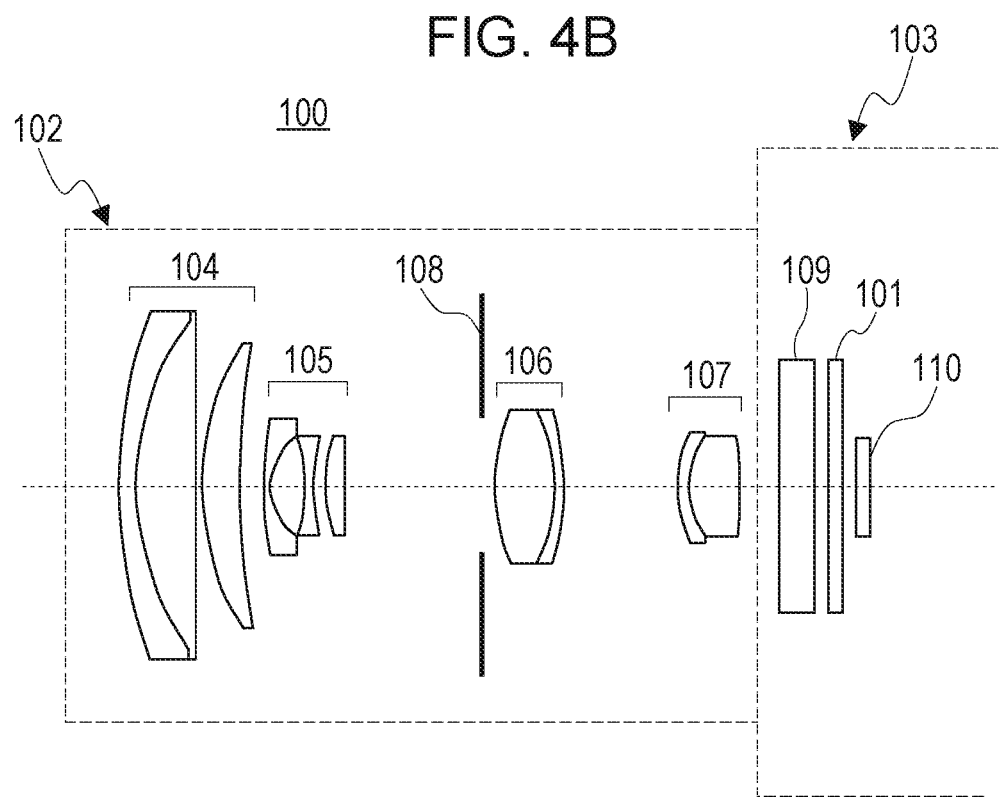
Figure 5A:
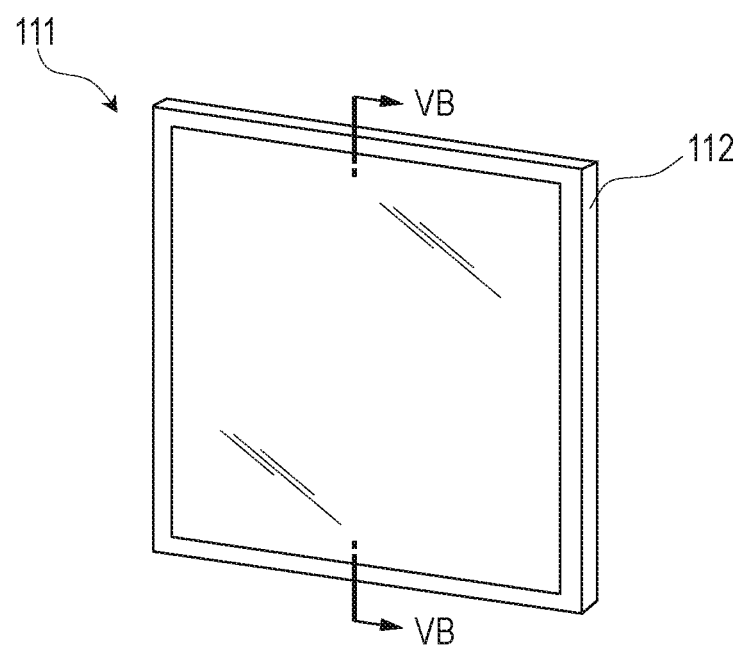
FIGS. 5A and 5B schematically illustrate an example of a structure of a window member according to a fifth embodiment.
Figure 5B:
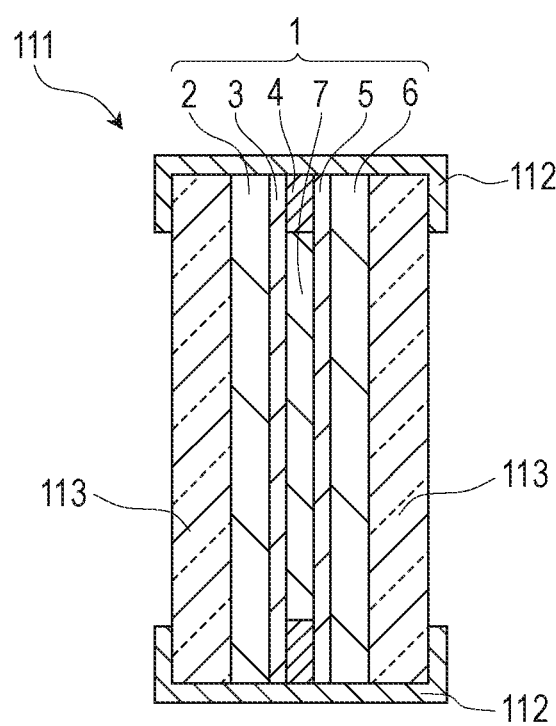

In the above-described structure of the image pickup apparatus 100, the optical filter 101 is disposed inside the lens unit 102, but is not limited thereto. As illustrated in FIG. 4B, the image pickup unit 103 may include the optical filter 101. In FIG. 4B, the optical filter 101 is disposed immediately in front of the light-receiving device 110. Any structure other than the above structures can be employed as long as the optical filter 101 is disposed at an appropriate position inside the image pickup unit 103 and the light-receiving device 110 is disposed so as to receive light that has passed through the optical filter 101. The optical filter 101 may be disposed at a position other than the position between the light-receiving device 110 and the glass block 109.

When the optical filter 101 is incorporated in the image pickup unit 103, the lens unit 102 itself connected to the image pickup unit 103 does not necessarily include the optical filter 101. Therefore, an image pickup apparatus capable of controlling light can be provided using a known lens unit.

The image pickup apparatus 100 according to this embodiment is applicable to products having a combination of the control of the amount of light and a light-receiving device. Examples of the products include cameras, digital cameras, video cameras, digital video cameras, and products including an image pickup apparatus therein, such as cellular phones, smart phones, PCs, and tablets.

The image pickup apparatus 100 according to this embodiment includes an optical filter including the EC device 1 according to the first embodiment that satisfies the formula (1) or the formula (2). Therefore, in the image pickup apparatus 100 according to this embodiment, the change in the absorption spectrum due to the change in the ambient temperature at which the EC device is driven can be reduced compared with the related art. That is, an image pickup apparatus whose temperature dependence is low can be provided.

In the image pickup apparatus 100 according to this embodiment, by using the optical filter 101 as a light-controlling member, the amount of light controlled can be appropriately changed with a single filter, which advantageously decreases the number of parts and saves space.

Fifth Embodiment

In this embodiment, a window member 111 that uses the EC device 1 according to the first embodiment will be

EXAMPLES

Example 1

Synthesis of Example Compound A-6

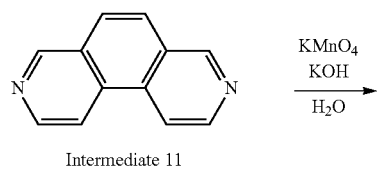

Intermediate 11

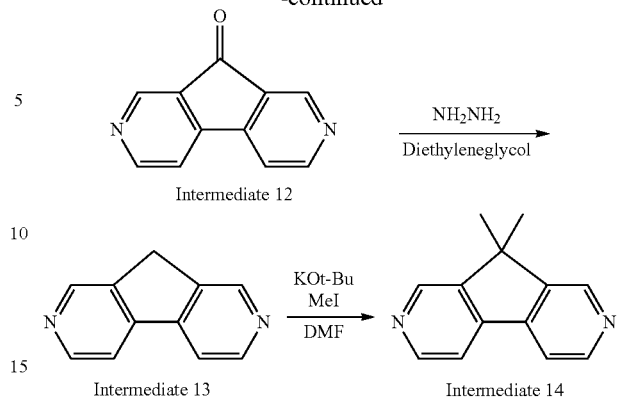

An intermediate 11 (13 g, 72 mmol) synthesized with reference to Angew. Chem. Int. Ed. 2007, 46, 198, potassium hydroxide (85%) (13.6 g, 240 mmol), and distilled water (100 mL) were charged into a reaction vessel and heated at a bath temperature of 90° C. Separately, distilled water (250 mL) and potassium permanganate (34 g, 215 mmol) were charged into a reaction vessel and heated to 90° C. to prepare a reddish purple solution. The solution was added dropwise to the solution prepared in advance using a cannular over about 5 minutes. The resulting mixture was heated under stirring at the same temperature for 1 hour. Then, a solid precipitated at an inner temperature of about 60° C. was filtered out. The filtrate was extracted with chloroform, and the organic layers were combined, sequentially washed with water and a saturated saline solution, dried, and concentrated to obtain a brown powder. The brown powder was subjected to column purification (eluent: chloroform/methanol=20/1) to obtain a yellow solid intermediate 12 (1.2 g, yield 9%).

The intermediate 12 (1.2 g, 6.6 mmol), diethylene glycol (12 mL), and hydrazine monohydrate (8.2 g, 163 mmol) were charged into a reaction vessel and heated under stirring at 100° C. for 12 hours. After the resulting dark reddish suspension was left to cool, water was added to the suspension. The suspension was extracted with dichloromethane, and the organic layers were combined, sequentially washed with water and a saturated saline solution, dried with anhydrous sodium sulfate, and concentrated to obtain a dark yellow solid. The dark yellow solid was subjected to column purification (eluent:ethyl acetate/methanol=10/1) to obtain a yellowish brown solid intermediate 13 (0.7 g, yield 79%).

The intermediate 13 (0.7 g, 4 mmol) and N,N-dimethylformamide (5 mL) were charged into a reaction vessel and cooled to 5° C. in an ice bath. Potassium tert-butoxide (1 g, 9 mmol) was added to the resulting solution and stirred at the same temperature for 30 minutes. Then, iodomethane (1.4 g, 10 mmol) diluted in N,N-dimethylformamide (5 mL) was added dropwise thereto. After the mixture was stirred at the same temperature for 30 minutes, the cooling bath was removed and the mixture was stirred at room temperature for 3 hours. The reddish brown suspension was added to a saturated sodium bicarbonate solution and extracted with ethyl acetate, and the organic layers were combined, sequentially washed with water and a saturated saline solution, dried with anhydrous sodium sulfate, and concentrated to obtain a dark yellow solid. The dark yellow solid was subjected to column purification (eluent:ethyl acetate/methanol=10/1) to obtain a beige solid intermediate 14 (0.2 g, yield 21%).

The intermediate 14 (98 mg, 0.5 mmol), methyl 4-(bromomethyl)benzoate (252 mg, 1.1 mmol), and 10 ml of acetonitrile were charged into a reaction vessel and stirred for 8 hours while being refluxed under heating. After completion of the reaction, the precipitated crystal was filtered and washed with acetonitrile to obtain 295 mg (yield: 90%) of an example compound A-6.

The structure of this compound was determined by NMR measurement.

$^1$H NMR (D$_2$O, 500 MHz) σ(ppm): 9.53 (s, 2H), 9.16 (d, 2H), 8.79 (d, 2H), 8.14 (d, 4H), 7.63 (d, 4H), 6.07 (s, 4H), 3.97 (s, 6H), 1.77 (s, 6H)

Example 2

Synthesis of Example Compound A-7

The example compound A-6 (200 mg, 0.3 mmol) was dissolved in water. An aqueous solution prepared by dissolving 500 mg of potassium hexafluorophosphate was added dropwise thereto and stirred at room temperature for 3 hours. The precipitated crystal was filtered and sequentially washed with isopropyl alcohol and diethyl ether to obtain 235 mg (yield: 98%) of an example compound A-7.

The structure of this compound was determined by NMR measurement.

$^1$H NMR (CD$_3$CN, 500 MHz) σ(ppm): 9.18 (s, 2H), 8.89 (d, 2H), 8.64 (d, 2H), 8.10 (d, 4H), 7.61 (d, 4H), 5.88 (s, 4H), 3.89 (s, 6H), 1.71 (s, 6H)

Example 3

Characteristic Evaluation of Example Compound A-7

In this Example, an EC device that uses the example compound A-7 was produced, and the characteristic evaluation of the example compound A-7 was performed. The structure of the EC device in this Example is the same as the structure of the EC device 1 in the above embodiment, and an EC medium contained in the EC layer 7 contains the example compound A-7. Tetrabutylammonium perchlorate serving as an electrolyte was dissolved in propylene carbonate at a concentration of 0.1 M, and then the example compound A-7 in Example 2 was dissolved therein at a concentration of 40.0 mM to obtain an EC medium.

Glass substrates with transparent conductive films (transparent electrode films) were used as the substrates 2 and 6 with the electrodes 3 and 5. An insulating layer (SiO$_2$) was formed in four end portions of the pair of glass substrates with transparent conductive films (ITO). A PET film (manufactured by Teijin DuPont Films Japan Limited, Melinex (registered trademark) S, 125 μm in thickness) serving as a spacer for specifying the distance between the substrates was placed between the pair of glass substrates with transparent electrode films. Then, the glass substrates and the PET film were bonded and sealed using an epoxy adhesive while an injection port for an EC medium was left. Thus, an empty cell with an injection port was produced.

Subsequently, the EC medium obtained by the above method was injected through the injection port by a vacuum injection method. Then, the injection port was sealed with an epoxy adhesive to produce an EC device.

The EC device just after the production had a transmittance of about 80% in the entire visible region, which showed high transparency.

Figure 10:
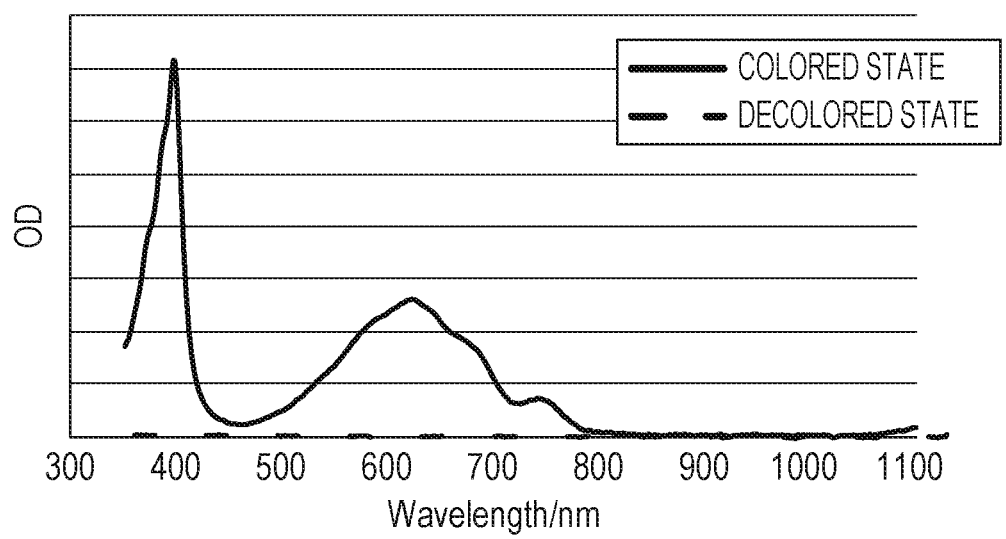
FIG. 10 illustrates ultraviolet-visible absorption spectra of an example compound A-7 in a colored state and a decolored state.

When a voltage of 3.0 V was applied to the EC device, absorption (λmax=397 nm, 623 nm) derived from reducing species of the example compound A-7 was observed and the EC device was colored in purple. When a voltage of –0.5 V was further applied, the EC device was decolored. This EC device can reversibly change between a colored state and a decolored state. FIG. 10 illustrates an ultraviolet-visible absorption spectrum (hereafter referred to as an "absorption spectrum") of the device produced in this Example. The light source was a DH-2000S deuterium halogen light source manufactured by Ocean Optics, Inc.

Example 4

Temperature Characteristic Evaluation of Example Compound A-7

Figure 11:
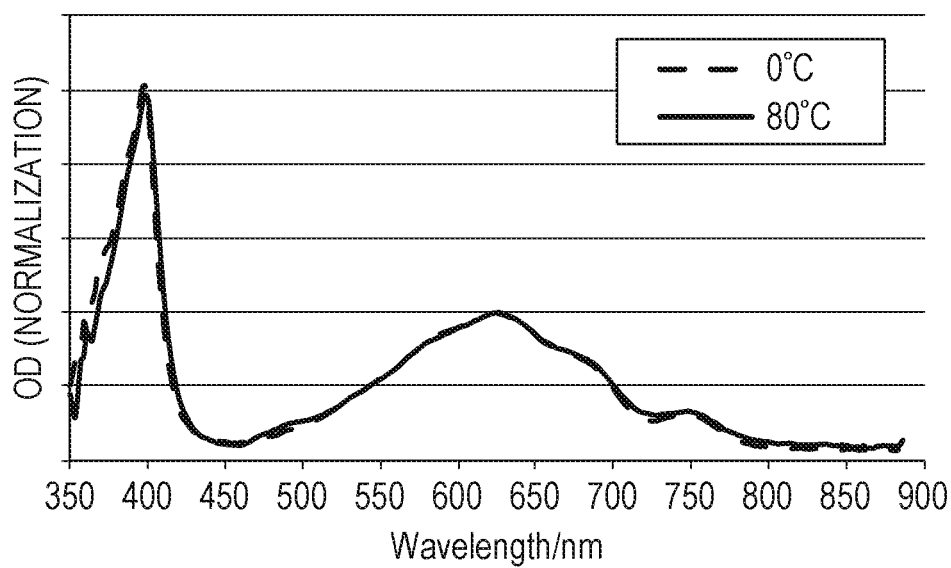
FIG. 11 illustrates ultraviolet-visible absorption spectra of an example compound A-7 in a colored state at 0° C. and 80° C.

For the EC device produced in Example 3, the absorption spectrum in a radically colored state was measured at ambient temperatures of 0° C. and 80° C. The obtained absorption spectra were normalized at 623 nm at which an absorption peak at 80° C. was observed. FIG. 11 illustrates the results. The shapes of the absorption spectra at 0° C. and 80° C. had only a small change. That is, the color change in a colored state at different temperatures is small, which shows that the color change due to ambient temperature does not readily occur in this EC device.

Comparative Example 1

For comparison, an EC device was produced in the same manner as in Example 3, except that a comparative compound 1 was used instead of the example compound A-7. For the produced EC device, the absorption spectrum in a radically colored state was measured at ambient temperatures of 0° C. and 80° C.

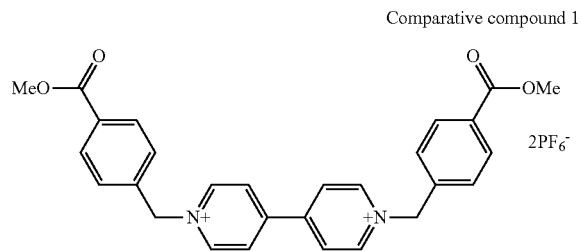 [SMILES: COC(=O)c1ccc(C[n+]2ccc(-c3cc[n+](Cc4ccc(C(=O)OC)cc4)cc3)cc2)cc1]

Comparative compound 1

Figure 12:
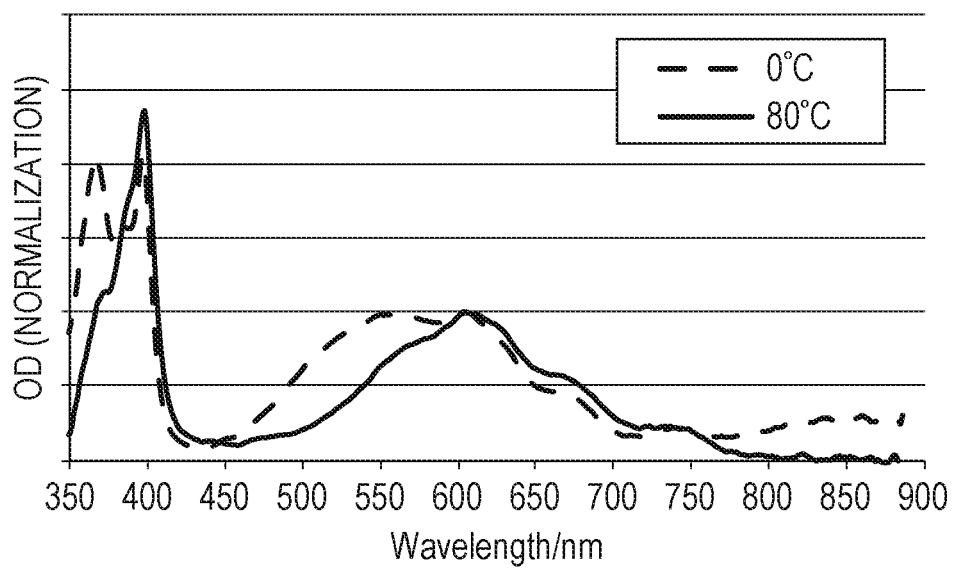
FIG. 12 illustrates ultraviolet-visible absorption spectra of a comparative compound 1 in a colored state at 0° C. and 80° C.
Figure 13:
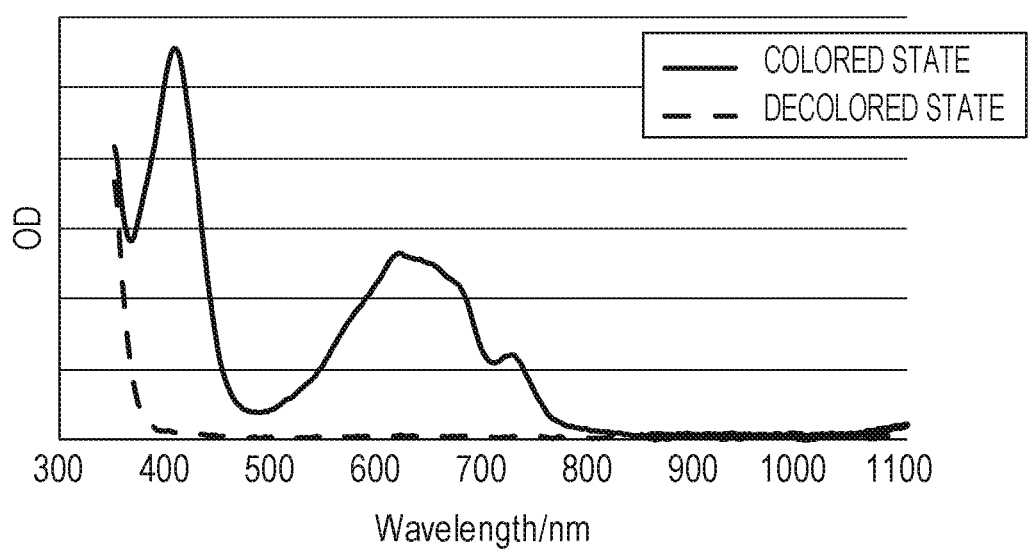
FIG. 13 illustrates ultraviolet-visible absorption spectra of an example compound A-15 in a colored state and a decolored state.

The obtained absorption spectra were normalized at 606 nm at which an absorption peak at 80° C. was observed. FIG. 12 illustrates the results. The shapes of the absorption spectra at 0° C. and 80° C. were considerably different. That is, the color change in a colored state at different ambient temperatures is large, which shows the color change due to ambient temperature.

Example 5

Synthesis of Example Compound A-5

An example compound A-5 was synthesized by the following method.

The intermediate 14 (98 mg, 0.5 mmol), 1-bromoheptane (268 mg, 1.5 mmol), and 10 ml of N,N-dimethylformamide were charged into a reaction vessel and stirred in a nitrogen stream at 100° C. for 8 hours. After completion of the reaction, the resulting precipitate was filtered and washed with ethyl acetate to obtain a light green powder. The obtained light green powder was dissolved in water. An aqueous solution prepared by dissolving 800 mg of sodium trifluoromethanesulfonate was added dropwise thereto and stirred at room temperature for 3 hours. The precipitated crystal was filtered and sequentially washed with isopropyl alcohol and diethyl ether to obtain 270 mg (yield: 78%) of an example compound A-5.

The structure of this compound was determined by NMR measurement.

$^1$H NMR (CD$_3$CN, 500 MHz) σ(ppm): 9.09 (s, 2H), 8.85 (d, 2H), 8.63 (d, 2H), 4.62 (t, 4H), 2.06 (m, 4H), 1.75 (s, 6H), 1.46-1.26 (m, 16H), 0.90 (t, 6H)

Example 6

Synthesis of Example Compound A-15

An example compound A-15 was synthesized by the following method.

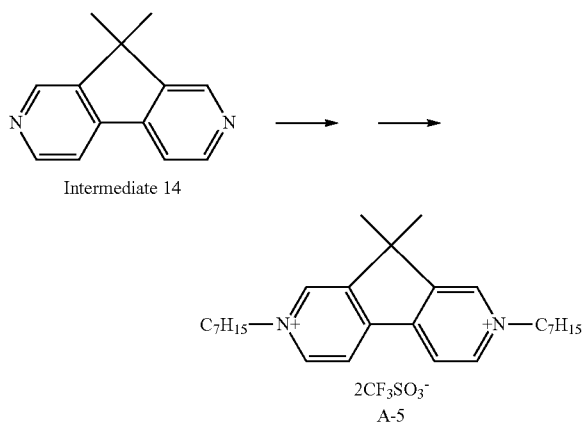

The intermediate 14 (963 mg, 4.91 mmol), 1-bromoheptane (895 mg, 5 mmol), and 10 ml of acetonitrile were charged into a reaction vessel and stirred in a nitrogen stream at 80° C. for 18 hours. After completion of the reaction, the resulting precipitate was filtered, washed with acetonitrile, and then subjected to column purification (eluent: methylene chloride/methanol=20/1) to obtain an intermediate 15 (1.32 g, yield 71%).

The intermediate 15 (1.32 g, 3.54 mmol), 2,4-dinitrobromobenzene (1.30 g, 5.26 mmol), and 10 ml of 2-propanol were charged into a reaction vessel and stirred in a nitrogen stream at 80° C. for 18 hours. After completion of the reaction, the resulting precipitate was filtered and washed with 2-propanol to obtain an intermediate 16 (1.56 g, yield 72%).

The intermediate 16 (808 g, 1.30 mmol), aniline (145 mg, 1.56 mmol), and 25 ml of ethanol were charged into a reaction vessel and stirred in a nitrogen stream at 80° C. for 12 hours. After completion of the reaction, the ethanol was removed in a vacuum and then ethyl acetate was added thereto to cause precipitation. Filtration was performed and the resulting crystal was dissolved in water. An aqueous solution prepared by dissolving 1 g of sodium trifluoromethanesulfonate was added dropwise thereto and stirring was performed at room temperature for 3 hours. The precipitated crystal was filtered and recrystallized with isopropyl alcohol to obtain 741 g (yield: 85%) of an example compound A-15.

The structure of this compound was determined by NMR measurement.

$^1$H NMR (DMSO, 500 MHz) σ(ppm): 10.01 (s, 1H), 9.76 (s, 1H), 9.63 (d, 1H), 9.37 (d, 1H), 9.15 (d, 1H), 9.09 (d, 1H), 7.99 (m, 2H), 7.83 (m, 3H), 4.70 (t, 2H), 2.04 (m, 2H), 1.78 (s, 6H), 1.46-1.26 (m, 8H), 0.87 (t, 3H)

Example 7

Characteristic Evaluation of Example Compound A-15

A device was produced in the same manner as in Example 3, except that the example compound A-15 was used instead of the example compound A-7 in Example 3. When a voltage of 3.0 V was applied to the device in this Example, absorption (λmax=408 nm, 621 nm) derived from reducing species of the example compound A-15 was observed and the EC device was colored in purple. When a voltage of −0.5 V was further applied, the EC device was decolored, which showed

Example 8

Synthesis of Example Compound A-19

An example compound A-19 was synthesized by the following method.

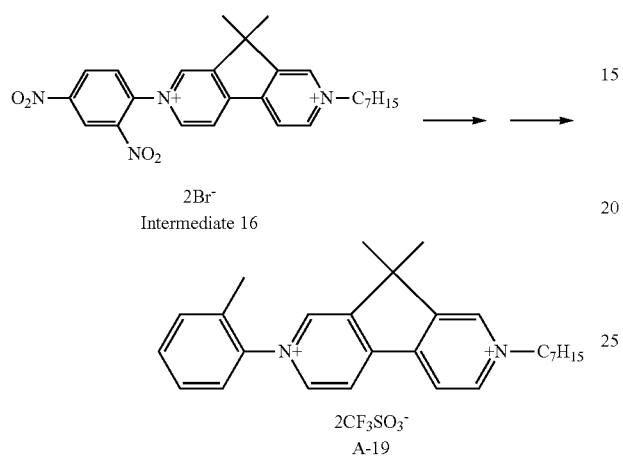

The intermediate 16 (734 g, 1.20 mmol), o-toluidine (154 mg, 1.44 mmol), and 25 ml of ethanol were charged into a reaction vessel and stirred in a nitrogen stream at 80° C. for 12 hours. After completion of the reaction, the ethanol was removed in a vacuum and then ethyl acetate was added thereto to cause precipitation. Filtration was performed and the resulting crystal was dissolved in water. An aqueous solution prepared by dissolving 1 g of sodium trifluoromethanesulfonate was added dropwise thereto and stirring was performed at room temperature for 3 hours. The precipitated crystal was filtered and recrystallized with isopropyl alcohol to obtain 667 g (yield: 83%) of an example compound A-19.

The structure of this compound was determined by NMR measurement.

$^1$H NMR (DMSO, 500 MHz) σ(ppm): 9.92 (s, 1H), 9.78 (s, 1H), 9.49 (d, 1H), 9.38 (d, 1H), 9.18 (d, 1H), 9.10 (d, 1H), 7.55-7.80 (m, 5H), 4.72 (t, 2H), 2.22 (s, 3H), 2.04 (m, 2H), 1.76 (s, 6H), 1.46-1.26 (m, 8H), 0.87 (t, 3H)

Example 9

Characteristic Evaluation of Example Compound A-19

Figure 14:
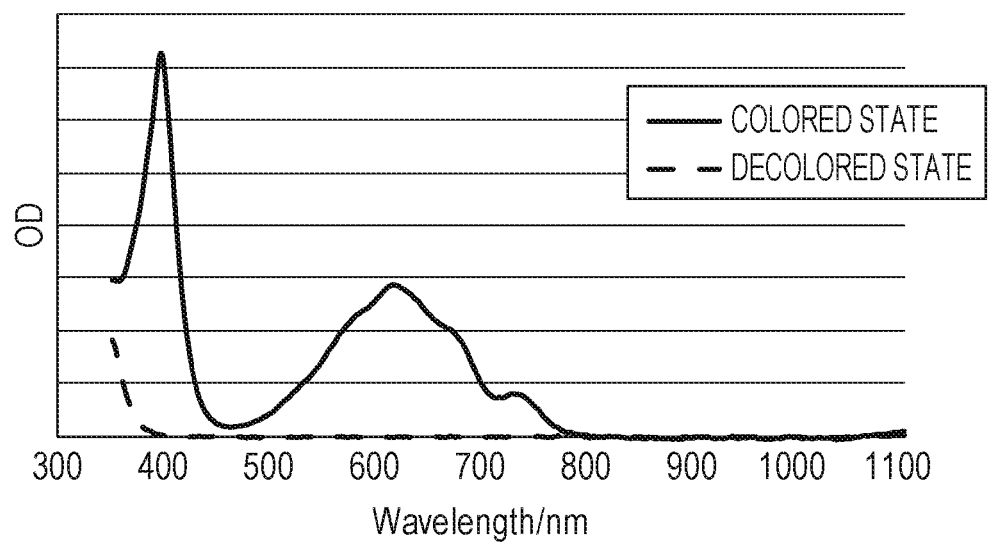
FIG. 14 illustrates ultraviolet-visible absorption spectra of an example compound A-19 in a colored state and a decolored state.

A device was produced in the same manner as in Example 3, except that the example compound A-19 was used instead of the example compound A-7 in Example 3. When a voltage of 3.0 V was applied to the device in this Example, absorption (λmax=397 nm, 617 nm) derived from reducing species of the example compound A-19 was observed and the EC device was colored in purple. When a voltage of −0.5 V was further applied, the EC device was decolored, which showed a reversible change between a colored state and a decolored state. FIG. 14 illustrates a coloring spectrum.

Example 10

Synthesis of Example Compound A-38

An example compound A-38 was synthesized by the following method.

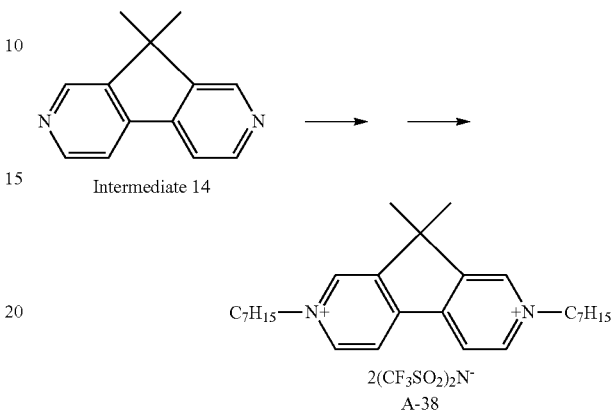

The intermediate 14 (98 mg, 0.5 mmol), 1-bromoheptane (268 mg, 1.5 mmol), and 10 ml of N,N-dimethylformamide were charged into a reaction vessel and stirred in a nitrogen stream at 100° C. for 8 hours. After completion of the reaction, the resulting precipitate was filtered and washed with ethyl acetate to obtain a light green powder. The obtained light green powder was dissolved in water. An aqueous solution prepared by dissolving 1.5 g of lithium bis(trifluoromethanesulfonyl)imide was added dropwise thereto and stirring was performed at room temperature for 3 hours. The precipitated crystal was filtered and sequentially washed with isopropyl alcohol and diethyl ether to obtain 382 mg (yield: 80%) of an example compound A-38.

The structure of this compound was determined by NMR measurement.

$^1$H NMR (CD$_3$CN, 500 MHz) σ(ppm): 9.09 (s, 2H), 8.85 (d, 2H), 8.63 (d, 2H), 4.62 (t, 4H), 2.06 (m, 4H), 1.75 (s, 6H), 1.46-1.26 (m, 16H), 0.90 (t, 6H)

Example 11

Characteristic Evaluation of Example Compound A-38

A device was produced in the same manner as in Example 3, except that the example compound A-38 was used instead of the example compound A-7 in Example 3. When a voltage of 3.0 V was applied to the device in this Example, absorption (λmax=394 nm, 621 nm) derived from reducing species of the example compound A-38 was observed and the EC device was colored in purple. When a voltage of −0.5 V was further applied, the EC device was decolored, which showed a reversible change between a colored state and a decolored state.

Example 12

Synthesis of Example Compound A-39

An example compound A-39 was produced by the following method.

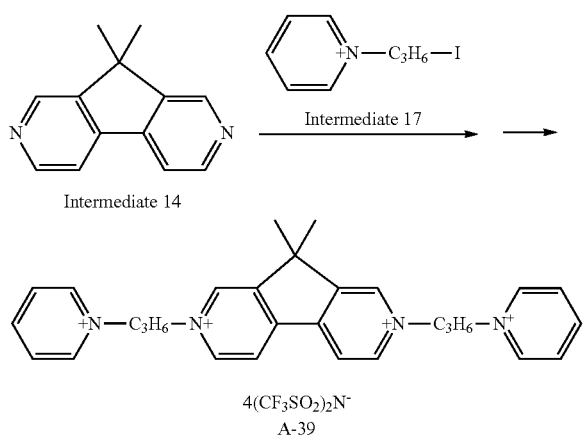

Example 14

Synthesis of Example Compound A-40

An example compound A-40 was synthesized by the following method.

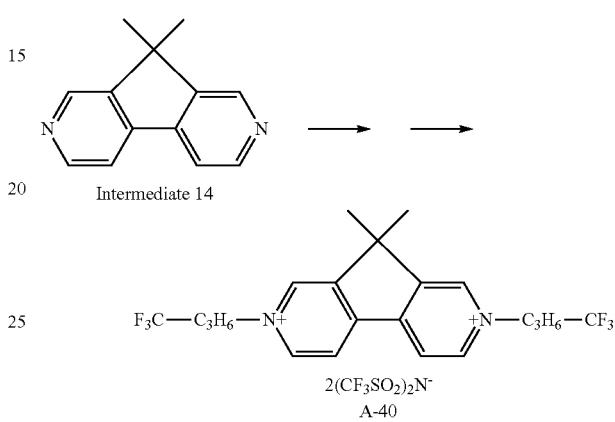

1,3-Diiodopropane (1.84 g, 4 mmol) and pyridine (158 mg, 2 mmol) were charged into a reaction vessel and stirred in a nitrogen stream at room temperature for 12 hours. After completion of the reaction, the resulting precipitate was filtered and washed with diisopropyl ether to obtain 446 mg (yield: 90%) of an intermediate 17.

The intermediate 14 (98 mg, 0.5 mmol), the intermediate 17 (372 mg, 1.5 mmol), and 10 ml of N,N-dimethylformamide were charged into a reaction vessel and stirred in a nitrogen stream at 100° C. for 8 hours. After completion of the reaction, ethyl acetate was added to the reaction solution. The resulting precipitate was filtered and washed with ethyl acetate to obtain a powder. The obtained powder was dissolved in water. An aqueous solution prepared by dissolving 3 g of lithium bis(trifluoromethanesulfonyl)imide was added dropwise thereto and stirring was performed at room temperature for 3 hours. The precipitated crystal was filtered and washed with diethyl ether to obtain 631 mg (yield: 81%) of an example compound A-39.

The structure of this compound was determined by NMR measurement.

$^1$H NMR (DMSO, 500 MHz) σ(ppm): 9.48 (s, 2H), 9.05 (d, 2H), 8.84 (d, 4H), 8.78 (d, 2H), 8.39 (t, 2H), 7.96 (t, 2H), 4.58-4.48 (m, 8H), 2.49 (m, 4H), 1.46 (s, 6H)

Example 13

Temperature Characteristic Evaluation of Example Compound A-39

A device was produced in the same manner as in Example 3, except that the example compound A-39 was used instead of the example compound A-7 in Example 3. When a voltage of 3.0 V was applied to the device in this Example, absorption (λmax=396 nm, 622 nm) derived from reducing species of the example compound A-39 was observed and the EC device was colored in purple. When a voltage of −0.5 V was further applied, the EC device was decolored, which showed a reversible change between a colored state and a decolored state.

Figure 15:
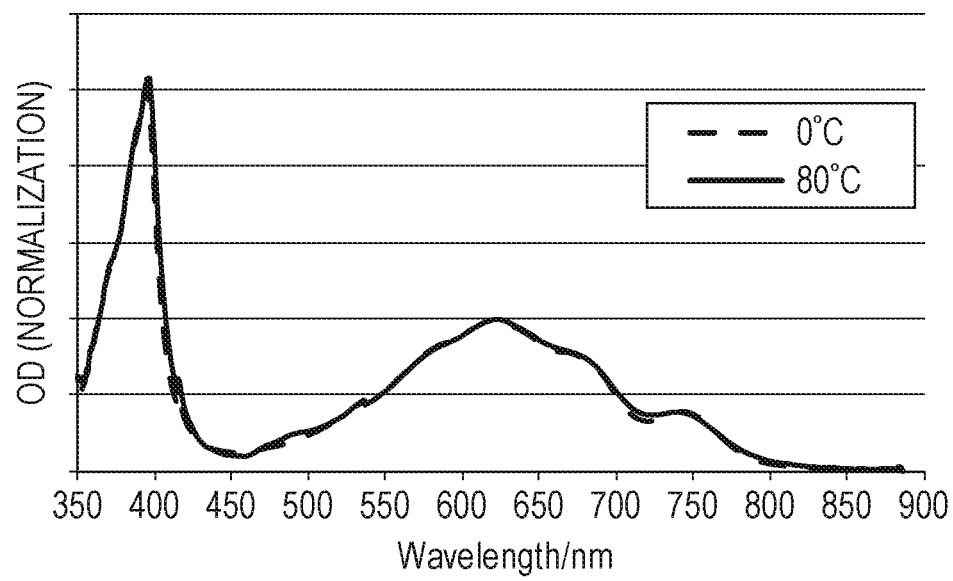
FIG. 15 illustrates ultraviolet-visible absorption spectra of an example compound A-40 in a colored state at 0° C. and 80° C.

For this EC device, the absorption spectrum in a radically colored state was measured at ambient temperatures of 0° C. and 80° C. The obtained absorption spectra were normalized at 622 nm at which an absorption peak at 80° C. was observed. FIG. 15 illustrates the results. The shapes of the absorption spectra at 0° C. and 80° C. had only a small change. That is, the color change in a colored state at different temperatures is small, which shows that the color change due to ambient temperature does not readily occur in this EC device.

Example 14

Synthesis of Example Compound A-40

An example compound A-40 was synthesized by the following method.

The intermediate 14 (294 mg, 1.5 mmol), 1,1,1-trifluoro-4-iodobutane (1.43 g, 6 mmol), and 10 ml of acetonitrile were charged into a reaction vessel and stirred in a nitrogen stream for 24 hours while being refluxed under heating. After completion of the reaction, ethyl acetate was added to the reaction solution. The resulting precipitate was filtered and washed with ethyl acetate to obtain a powder. The obtained powder was dissolved in water. An aqueous solution prepared by dissolving 5 g of lithium bis(trifluoromethanesulfonyl)imide was added dropwise thereto and stirring was performed at room temperature for 3 hours. The precipitated crystal was filtered and sequentially washed with isopropyl alcohol and diethyl ether to obtain 930 mg (yield: 63%) of an example compound A-40.

The structure of this compound was determined by NMR measurement.

$^1$H NMR (CD$_3$CN, 500 MHz) σ(ppm): 9.14 (s, 2H), 8.89 (d, 2H), 8.68 (d, 2H), 4.71 (t, 4H), 2.46-2.33 (m, 8H), 1.78 (s, 6H)

Example 15

Characteristic Evaluation of Example Compound A-40

A device was produced in the same manner as in Example 3, except that the example compound A-40 was used instead of the example compound A-7 in Example 3. When a voltage of 3.0 V was applied to the device in this Example, absorption (λmax=395 nm, 623 snm) derived from reducing species of the example compound A-40 was observed and the EC device was colored in purple. When a voltage of −0.5 V was further applied, the EC device was decolored, which showed a reversible change between a colored state and a decolored state.

Example 16

Synthesis of Example Compound A-41

An example compound A-41 was synthesized by the following method.

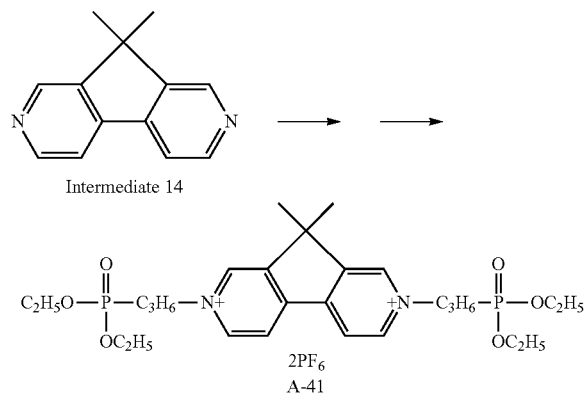

The intermediate 14 (98 mg, 0.5 mmol), diethyl (3-bromopropyl)phosphonate (389 mg, 1.5 mmol), and 10 ml of N,N-dimethylformamide were charged into a reaction vessel and stirred in a nitrogen stream at 100° C. for 8 hours. After completion of the reaction, ethyl acetate was added to the reaction solution. The resulting precipitate was filtered, washed with ethyl acetate to obtain a powder. The obtained powder was dissolved in water. An aqueous solution prepared by dissolving 1 g of potassium hexafluorophosphate was added dropwise thereto and stirring was performed at room temperature for 3 hours. The precipitated crystal was filtered and sequentially washed with isopropyl alcohol and diethyl ether to obtain 317 mg (yield: 75%) of an example compound A-41.

The structure of this compound was determined by NMR measurement.

$^1$H NMR (CD$_3$CN, 500 MHz) σ(ppm): 9.14 (s, 2H), 8.89 (d, 2H), 8.65 (d, 2H), 4.73 (t, 4H), 4.06 (m, 8H), 2.33 (m, 4H), 1.90-1.78 (m, 4H), 1.75 (s, 6H), 1.29 (m, 12H)

Example 17

In this Example, an example of a complementary EC device 1 that uses an organic compound serving as a cathode material and represented by the general formula (2) and an anode material will be described.

The EC device 1 in this Example has the same structure as illustrated in FIG. 1. Two ITO substrates obtained by forming electrodes 3 and 5 made of ITO on the respective surfaces of substrates 2 and 6 made of glass are bonded to each other with 50 μm spacers 4 disposed therebetween. An EC layer 7 is disposed in a gap defined by the substrates 2 and 6 and the spacers 4.

The EC layer 7 has a complementary solution structure including 5,10-dimethyl-5,10-dihydrophenazine (hereafter referred to as DMDHP) serving as an anode EC material and one bipyridine derivative serving as a cathode EC material. Herein, it has been confirmed from the temperature characteristic evaluation on a single material that the shape of the absorption spectrum of DMDHP substantially does not change with the ambient temperature.

In this Example, the example compound A-7 was used as a bipyridine derivative, and one anodic EC material was combined with one cathodic EC material. A solution prepared by dissolving DMDHP and the example compound A-7 in a propylene carbonate solvent was injected into the EC device 1. Since the example compound A-7 serving as a viologen derivative has PF$_6^-$ as a counterion, another material was not added as an electrolyte. The concentration of each of DMDHP and the bipyridine derivative was 100 mM.

At each of ambient temperatures of 0° C., 25° C., 50° C., and 80° C., the produced EC device was driven to change its state from a decolored state to a colored state, and the absorption spectrum in a colored state was measured. The drive voltage was 0.6 V and a direct-current voltage with a duty ratio of 100% was applied. The absorption spectrum was measured five seconds after the driving and the decolored state was treated as a zero baseline.

In the evaluation of the EC device 1, the drive voltage was applied with a potentiostat (CellTest 1470E) manufactured by Solartron and the spectrum was measured with a spectroscope (USB2000-UV-VIS) manufactured by Ocean Optics, Inc. The change in absorbance of the EC material with application of voltage was measured at 1 scan/sec. The measurement sample, electric wiring, and optical fiber cables were introduced into an environmental test chamber manufactured by Horiba Espec. The electrical characteristics and the absorption spectrum were measured in a controlled temperature range of 0° C. to 80° C.

Figure 3A:
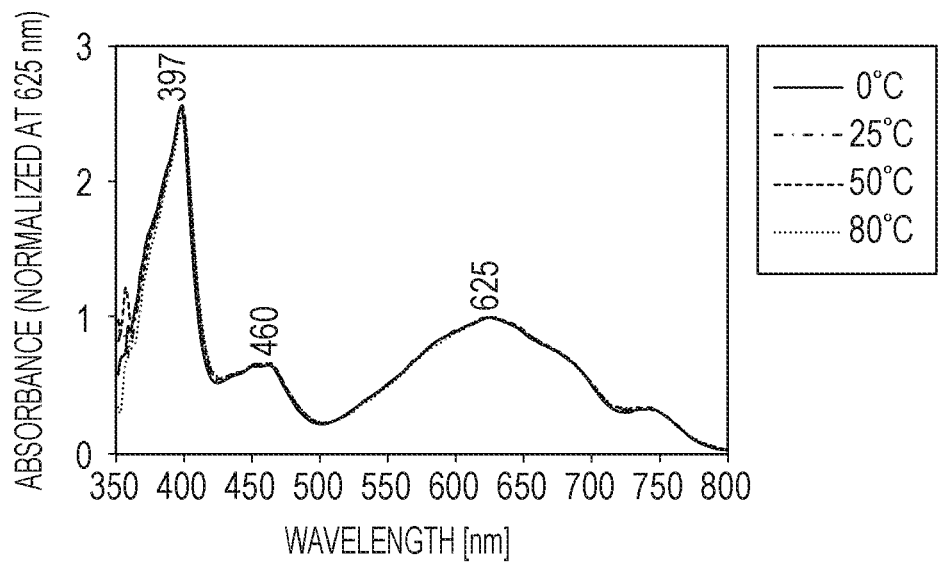
FIGS. 3A and 3B illustrate spectra of electrochromic devices in Example 17 and Comparative Example 2 at different ambient temperatures.

FIG. 3A illustrates a spectrum obtained by normalizing the absorption spectrum in a colored state at each ambient temperature with respect to the radical absorption peak of the bipyridine derivative. Specifically, FIG. 3A illustrates a spectrum related to the EC device 1 that uses the example compound A-7 as a bipyridine derivative, the spectrum being obtained by normalizing the absorption spectrum in a colored state at each ambient temperature with respect to the absorption peak at a wavelength of 625 nm.

As is clear from FIG. 3A, in the case of the EC device 1 that uses the example compound A-7, the spectra have substantially the same shape at each ambient temperature. These results suggest that the ratio of monomer and associate of the example compound A-7 does not easily change with the ambient temperature. In FIG. 3A, the absorption at 460 nm is derived from DMDHP, the absorption at 397 nm is derived from n-π* transition of monomers of the example compound A-7, and the absorption at 625 nm is derived from π-π* transition of monomers of a compound 1. In the EC device 1 containing the example compound A-7, it is found that the absorption intensity ratio does not significantly change even if the ambient temperature changes from 0° C. to 80° C.

Figure 7:
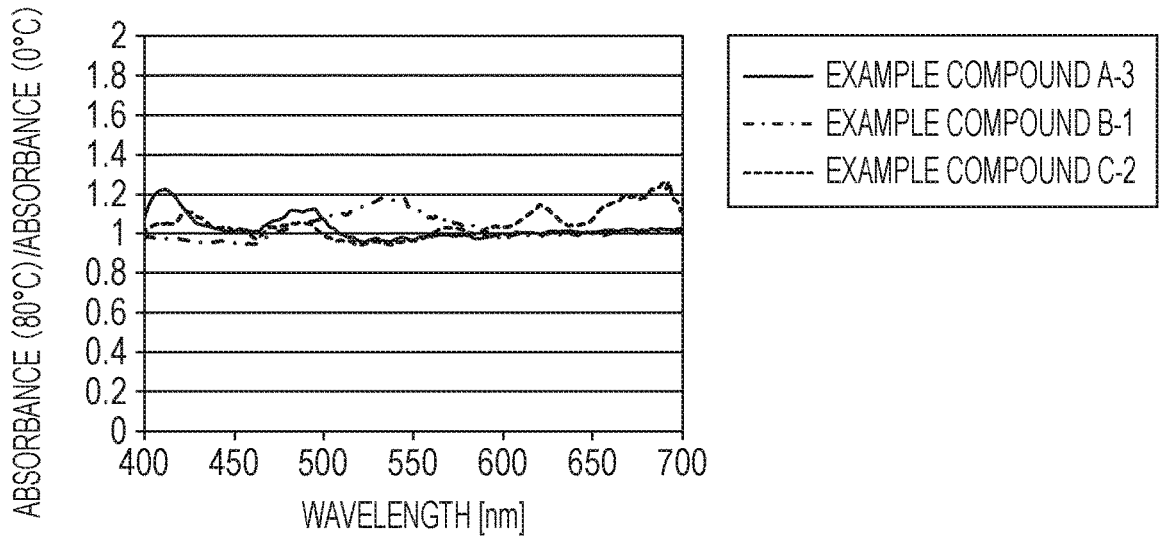
FIG. 7 illustrates absorbance ratios of electrochromic devices in Examples 17 and 18.

FIG. 7 illustrates an absorbance ratio (f2/f1) regarding the EC device 1 containing the example compound A-7. Specifically, FIG. 7 illustrates a spectrum obtained by dividing a spectrum (f2) by a spectrum (f1) regarding the EC device in this Example, where the spectrum (f2) is obtained by normalizing the absorption spectrum of each compound at an ambient temperature of 80° C. and the spectrum (f1) is obtained by normalizing the absorption spectrum of each compound at an ambient temperature of 0° C. In FIG. 7, the result related to the EC device 1 in this Example that contains the example compound A-7 is indicated by a solid line.

The useful wavelength range for typical optical filters used in a visible region is 450 nm to 650 nm. In FIG. 7, the ratio f2/f1 at any wavelength m in this wavelength range is a ratio (absorbance ratio) f2(m)/f1(m) of the absorbance f2(m) at the wavelength m in the spectrum f2 to the absorbance f1(m) at the wavelength m in the spectrum f1.

The EC device 1 that uses the example compound A-7 has an absorbance ratio f2(m)/f1(m) of more than 0.8 and less than 1.2, which satisfies the formula (1), at any wavelength in the wavelength range of 450 nm to 650 nm. Furthermore, the EC device 1 that uses the example compound A-7 satisfies the formula (2). The EC device 1 containing a bipyridine derivative that satisfies the formula (1) has only a small change in absorption spectrum due to ambient temperature. When the bipyridine derivative that satisfies the formula (1) is used as an EC material, the change in the shape of the absorption spectrum of an EC device due to a change in ambient temperature can be reduced.

As described above, according to the EC device 1 in this Example, the change in the absorption spectrum of the EC device due to the change in the ambient temperature at which the EC device is driven can be reduced compared with the related art. That is, an EC device whose temperature dependence is low can be provided.

Example 18

In this Example, the temperature characteristics of the EC device 1 that uses an organic compound represented by the general formula (2) will be described. Specifically, in this Example, the temperature characteristics of each of an EC device that uses an example compound B-1 and an EC device that uses an example compound C-2 will be described as those of the EC device 1 that uses an organic compound represented by the general formula (2).

In the EC device in this Example, DMDHP is used as an anode EC material and the example compound B-1 or the example compound C-2 is used as a cathode material. DMDHP and each of the bipyridine derivatives are dissolved in a propylene carbonate solvent so as to have a concentration of 100 mM. The EC device in this Example is produced by the same method as that of the EC device in Example 17, except that the bipyridine derivative serving as a cathode material is the example compound B-1 or C-2.

For the EC devices in this Example, the absorption spectrum was measured at different ambient temperatures by the same method as that in Example 17.

Figure 6A:
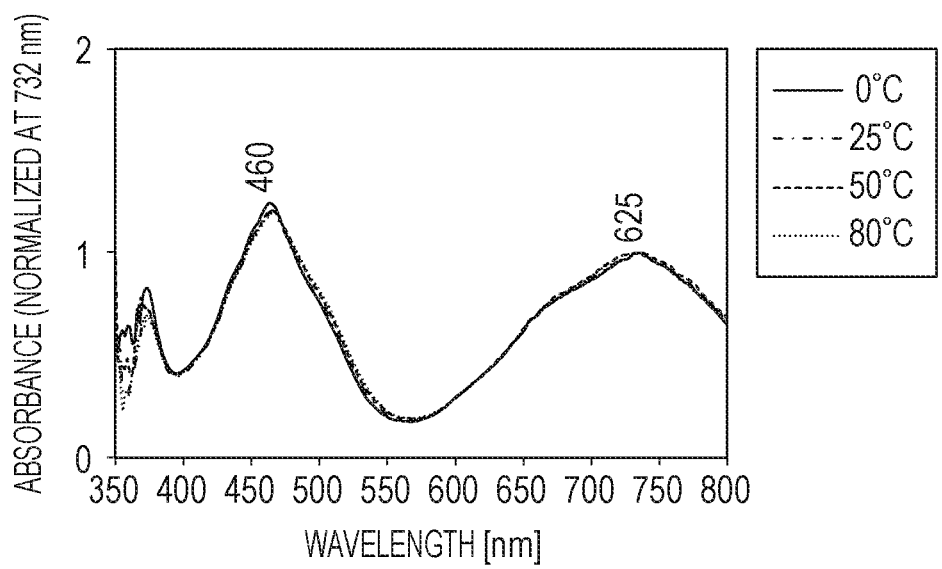
FIGS. 6A and 6B illustrate absorption spectra of an electrochromic device in Example 18 at different ambient temperatures.
Figure 6B:
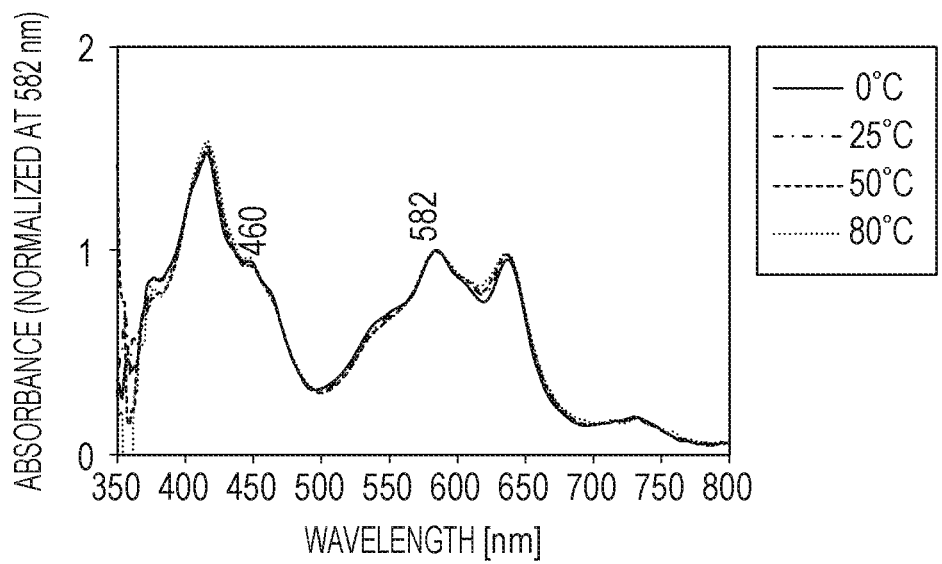

FIGS. 6A and 6B illustrate a spectrum obtained by normalizing the absorption spectrum obtained by driving each EC device in this Example at each ambient temperature with respect to the radical absorption peak of the bipyridine derivative. FIG. 6A illustrates a spectrum related to the EC device that uses DMDHP and the example compound B-1, the spectrum being normalized with respect to the radical absorption peak at a wavelength of 732 nm. FIG. 6B illustrates a spectrum related to the EC device that uses DMDHP and the example compound C-2, the spectrum being normalized with respect to the radical absorption peak at a wavelength of 582 nm.

As is clear from FIGS. 6A and 6B, in the EC device that uses the example compound B-1 or the example compound C-2, the shape of the absorption spectrum does not significantly change even if the ambient temperature changes. These results show that, as in Example 17, the example compound B-1 and the example compound C-2 have only a small change in the ratio of monomer and associate even if the ambient temperature changes. In other words, in each of the example compounds B-1 and C-2, the associate is not easily formed and the form of monomer is easily maintained even if the ambient temperature changes.

FIG. 7 illustrates an absorbance ratio (f2/f1) regarding the EC device containing any one of the example compounds B-1 and C-2 and the example compound A-7 in Example 17. Specifically, FIG. 7 illustrates a spectrum obtained by dividing a spectrum (f2) by a spectrum (f1) regarding each EC device in this Example, where the spectrum (f2) is obtained by normalizing the absorption spectrum of each compound at an ambient temperature of 80° C. and the spectrum (f1) is obtained by normalizing the absorption spectrum of each compound at an ambient temperature of 0° C.

Each of the EC devices has an absorbance ratio f2(m)/f1(m) of more than 0.8 and less than 1.2, which satisfies the formula (1), at any wavelength m in the wavelength range of 450 nm to 650 nm. Each of the EC devices also satisfies the formula (2). When the bipyridine derivative that satisfies the formula (1) is used for EC devices, the change in the shape of the absorption spectrum of an EC device due to a change in ambient temperature can be reduced.

According to the EC device in this Example, the change in the absorption spectrum of the EC device due to the change in the ambient temperature at which the EC device is driven can be reduced compared with the related art. That is, an EC device whose temperature dependence is low can be provided.

As described in this Example, the bipyridine derivative having a structure represented by the general formula (2) has only a small change in absorption spectrum due to ambient temperature and thus is suitable for use in organic EC devices.

Example 19

In this Example, the temperature characteristics of the EC device 1 that uses an organic compound represented by the general formula (5) will be described. Specifically, in this Example, the temperature characteristics of an EC device that uses an example compound D-1 will be described as those of the EC device 1 that uses an organic compound represented by the general formula (5).

In the EC device in this Example, DMDHP is used as an anode EC material and the example compound D-1 is used as a cathode material. DMDHP and the bipyridine derivative are dissolved in a propylene carbonate solvent so as to have a concentration of 100 mM. The EC device in this Example is produced by the same method as that of the EC device in Example 17, except that the bipyridine derivative serving as a cathode material is the example compound D-1.

For the EC device in this Example, the absorption spectrum was measured at different ambient temperatures by the same method as that in Examples.

Figure 9:
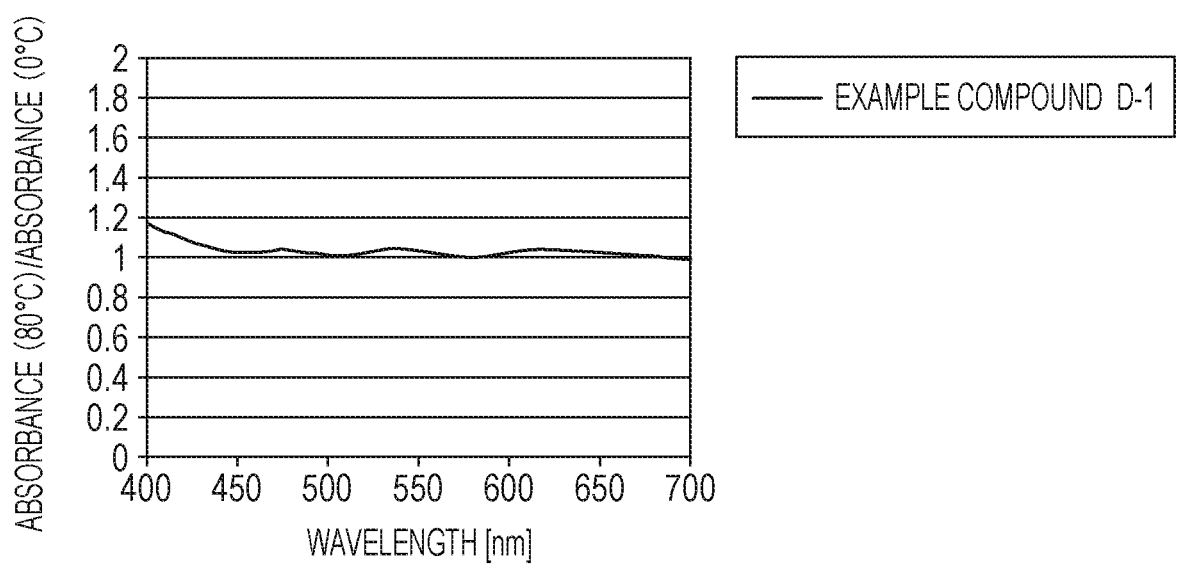
FIG. 9 illustrates an absorbance ratio of an electrochromic device in Example 19.

FIG. 9 illustrates an absorbance ratio (f2/f1) regarding the EC device that uses the example compound D-1. Specifically, FIG. 9 illustrates a spectrum obtained by dividing a spectrum (f2) by a spectrum (f1) regarding the EC device in this Example, where the spectrum (f2) is obtained by normalizing the absorption spectrum at an ambient temperature of 80° C. and the spectrum (f1) is obtained by normalizing the absorption spectrum at an ambient temperature of 0° C.

As is clear from FIG. 9, the EC device in this Example has an absorbance ratio f2(m)/f1(m) of more than 0.8 and less than 1.2, which satisfies the formula (1) and the formula (2), at any wavelength m in the wavelength range of 450 nm to 650 nm. When the bipyridine derivative that satisfies the formula (1) is used for EC layers, the change in the shape of the absorption spectrum of an EC device due to a change in ambient temperature can be reduced.

According to the EC device in this Example, the change in the absorption spectrum of the EC device due to the change in the ambient temperature at which the EC device is driven can be reduced compared with the related art. That is, an EC device whose temperature dependence is low can be provided.

As described in this Example, the bipyridine derivative having a structure represented by the general formula (5) has only a small change in absorption spectrum due to ambient temperature and thus is suitable for use in organic EC devices.

Comparative Example 2

In Comparative Example 2, EC devices that use, as EC materials, comparative compounds 2 to 7 not represented by the general formulae (1) to (5) will be described.

The comparative compounds 6 and 7 each have a structure in which bipyridine derivatives are bonded to each other via a substituent. The comparative compound 7 has a ring structure constituted by two bipyridine derivatives. Such a compound having bipyridine derivatives bonded to each other very easily causes association, and the absorbance of associate is higher than that of monomer even at room temperature. In such a material, the absorbance of associate tends to decrease and the absorbance of monomer tends to increase as the temperature increases. This is believed to be because the association state is lost through thermal molecular vibration.

EC devices were produced using the comparative compounds 2 to 7 by using the same structure and method as those in Example 17. The EC devices that use the comparative compounds 2 to 7 are the same as the EC devices 1 in Examples 17 to 19, except that the comparative compounds 2 to 7 are used as bipyridine derivatives.

Comparative compound 2

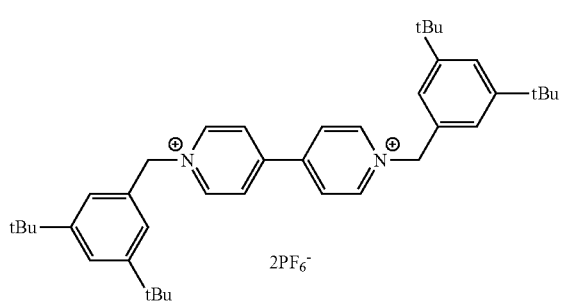

2PF$_6^-$

Comparative compound 3

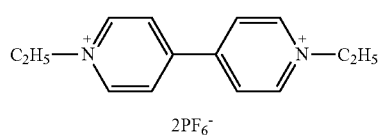

2PF$_6^-$

Comparative compound 4

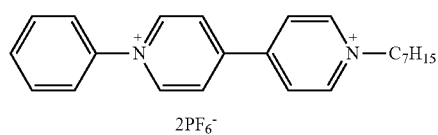

2PF$_6^-$

-continued

Comparative compound 5

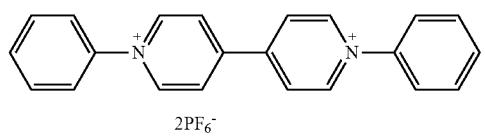

2PF$_6^-$

Comparative compound 6

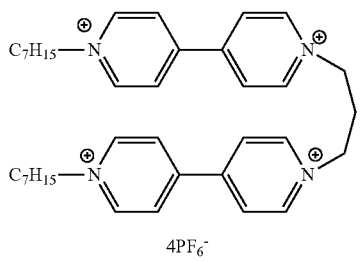

4PF$_6^-$

Comparative compound 7

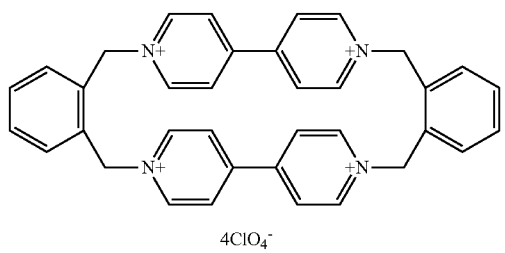

4ClO$_4^-$

Figure 3B:
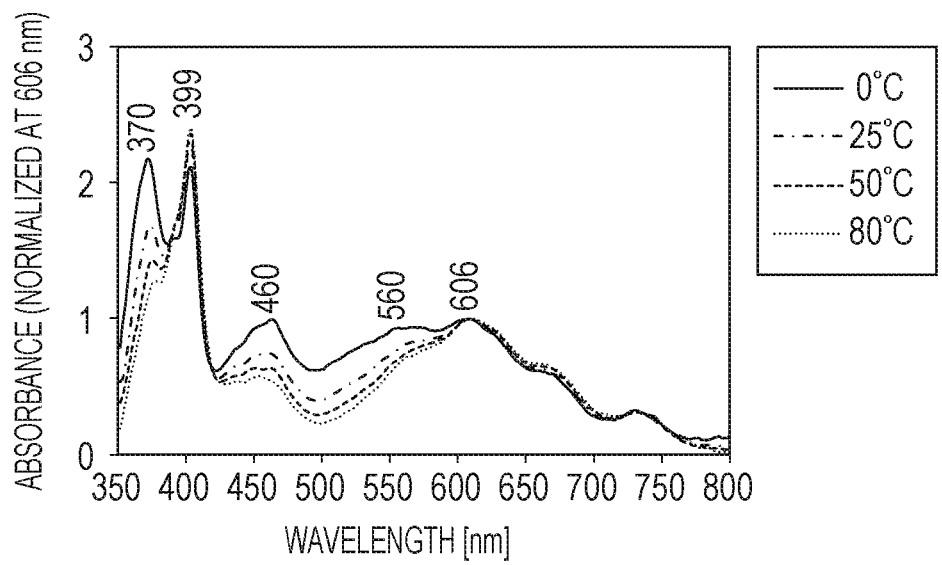

FIG. 3B illustrates a spectrum obtained by normalizing the absorption spectrum of an EC device that uses a comparative compound 2 in a colored state at each ambient temperature with respect to the radical absorption peak of the bipyridine derivative. Specifically, FIG. 3B illustrates a spectrum related to the EC device that uses the comparative compound 2 as a bipyridine derivative, the spectrum being obtained by normalizing the absorption spectrum in a colored state at each ambient temperature with respect to the absorption peak at a wavelength of 606 nm.

As is clear from FIG. 3A, in the case of the EC device 1 that uses the example compound A-7, the spectra have substantially the same shape at each ambient temperature. In contrast, as is clear from FIG. 3B, in the case of the EC device that uses the comparative compound 2, the absorption spectra have different shapes at each temperature. These results show that the ratio of monomer and associate of the comparative compound 2 considerably changes with the ambient temperature.

The absorption peaks of a monomer of the comparative compound 2 appear at wavelengths of 399 nm and 606 nm, and other absorption peaks appear at shorter wavelengths of 370 nm and 560 nm. These peaks are generated as a result of formation of an associate of the comparative compound 2. The form of associate is generally more stable than the form of monomer in terms of electronic state, and therefore the absorption wavelength shifts to shorter wavelengths (high energy). That is, it is believed that the absorption wavelength 399 nm of a monomer shifts to the absorption wavelength 370 nm of an associate and the absorption wavelength 606 nm of a monomer shifts to the absorption wavelength 560 nm of an associate.

Figure 8:
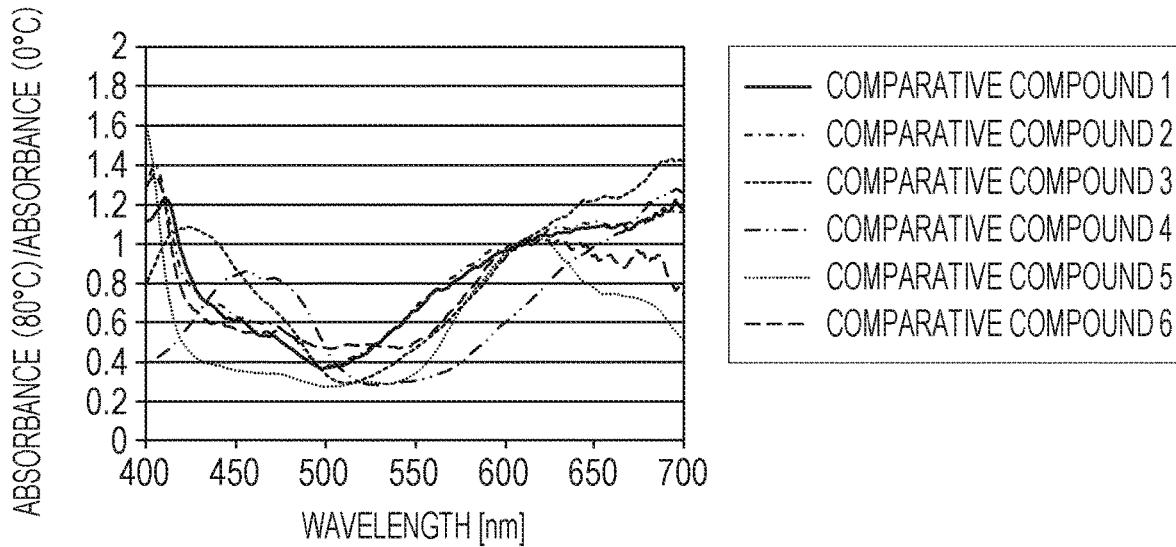
FIG. 8 illustrates absorbance ratios of electrochromic devices in Comparative Example 2.

FIG. 8 illustrates a value (f2/f1) obtained by dividing a spectrum (f2) by a spectrum (f1) regarding the EC devices that use the comparative compounds 2 to 7, where the spectrum (f2) is obtained by normalizing the absorption spectrum at an ambient temperature of 80° C. and the spectrum (f1) is obtained by normalizing the absorption spectrum at an ambient temperature of 0° C.

At any wavelength m in the wavelength range of 450 nm to 650 nm, which is useful for typical optical filters in a visible region, the absorbance ratio of the absorbance f2(m) in the spectrum f2 to the absorbance f1(m) in the spectrum f1 does not satisfy the formula (1). In FIG. 8, even the comparative compound having the smallest absorbance ratio has a relational expression of 0.5<f2(m)/f1(m)<1.5 in the wavelength range of 450 nm to 650 nm.

As described above, the EC devices that use the comparative compounds 2 to 7 serving as bipyridine derivatives have a large change in absorption spectrum due to a change in ambient temperature and are not suitable as EC devices whose temperature dependence is low.

As is clear from the comparison with Examples 17 to 19, a change in the ratio of monomer and associate due to ambient temperature is dependent on the structure of the bipyridine derivative. As described above, as a result of the studies conducted by the present inventors, the organic compounds represented by the general formulae (1) to (5) have only a small change in the existence ratio of monomer and associate due to ambient temperature and thus can be provided for EC devices whose temperature dependence is low.

In the organic compound or electrochromic device according to one aspect of the present invention, the change in the absorption spectrum in a colored state at different ambient temperatures can be reduced compared with the related art.

The present invention is not limited to the above embodiments, and various changes and modifications can be made without departing from the spirit and scope of the present invention. Accordingly, the following claims are attached to disclose the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An organic compound represented by general formula (1) below:

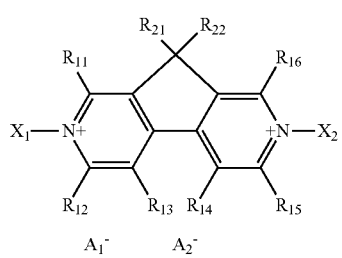

(1)

where $X_1$ and $X_2$ are each independently selected from the group consisting of an alkyl group optionally having a substituent, an aryl group optionally having a substituent, and an aralkyl group optionally having a substituent;

$R_{11}$ to $R_{16}$ are each independently selected from the group consisting of a hydrogen atom, an alkyl group optionally having a substituent, an alkoxy group optionally having a substituent, an aryl group optionally having a substituent, a heterocyclic group optionally having a substituent, and a halogen atom; $R_{21}$ and $R_{22}$ are each independently selected from the group consisting of a hydrogen atom, an alkyl group optionally having a substituent, an aryl group optionally having a substituent, and an aralkyl group optionally having a substituent; and $A_1^-$ and $A_2^-$ each independently represent a monovalent anion.

2. The organic compound according to claim 1, wherein $R_{11}$ to $R_{16}$ each represent a hydrogen atom.

3. The organic compound according to claim 1, wherein $A_1^-$ and $A_2^-$ represent the same anion.

4. An electrochromic device comprising a pair of electrodes and an electrochromic layer disposed between the pair of electrodes,
wherein the electrochromic layer contains the organic compound according to claim 1.

5. The electrochromic device according to claim 4, wherein the electrochromic layer contains an organic compound other than the organic compound.

6. The electrochromic device according to claim 4, wherein the other organic compound is a phenazine compound, ferrocene, a metallocene compound, a phenylenediamine compound, or a pyrazoline compound.

7. The electrochromic device according to claim 4, wherein the electrochromic layer contains a liquid containing an electrolyte and an organic EC compound.

8. An electrochromic apparatus comprising:
the electrochromic device according to claim 4; and
driving means for driving the electrochromic device.

9. An optical filter comprising:
electrochromic device according to claim 4; and
an active device connected to the electrochromic device.

10. An image pickup apparatus comprising:
an image pickup optical system including a plurality of lenses;
optical filter according to claim 9; and
a light-receiving device configured to receive light that has passed through the optical filter.

11. A window member comprising:
a pair of substrates;
the electrochromic device according to claim 4, the electrochromic device being disposed between the pair of substrates; and
an active device connected to the electrochromic device,
wherein the electrochromic device is configured to control an amount of light that passes through the pair of substrates.

* * * * *